(12) United States Patent
Papageorgiou et al.

(10) Patent No.: US 10,380,645 B2
(45) Date of Patent: Aug. 13, 2019

(54) SYSTEM FOR SECURELY TRANSMITTING MEDICAL RECORDS AND FOR PROVIDING A SPONSORSHIP OPPORTUNITY

(71) Applicant: DO-THEDOC Inc., Ann Arbor, MI (US)

(72) Inventors: Dimitris S. Papageorgiou, Ann Arbor, MI (US); Steven E. Holodnick, Ann Arbor, MI (US); Kyle T. Racine, Ann Arbor, MI (US); Igor O. Goryushin, Troitsk (RU)

(73) Assignee: DO-THEDOC INC., Ann Arbor, MI (US)

( * ) Notice: Subject to any disclaimer, the term of this patent is extended or adjusted under 35 U.S.C. 154(b) by 937 days.

(21) Appl. No.: 14/641,115

(22) Filed: Mar. 6, 2015

(65) Prior Publication Data

US 2015/0254727 A1     Sep. 10, 2015

Related U.S. Application Data

(60) Provisional application No. 61/949,656, filed on Mar. 7, 2014.

(51) Int. Cl.
*G06Q 30/02* (2012.01)
*G16H 10/60* (2018.01)

(52) U.S. Cl.
CPC ......... *G06Q 30/0269* (2013.01); *G16H 10/60* (2018.01)

(58) Field of Classification Search
CPC ............. A61M 2230/30; A61M 5/1407; G06F 19/3418; G06F 19/324; G06F 19/325; G06F 19/328
See application file for complete search history.

(56) References Cited

U.S. PATENT DOCUMENTS

| 6,141,010 A | 10/2000 | Hoyle |
| 6,182,050 B1 | 1/2001 | Ballard |
| 6,332,127 B1 | 12/2001 | Bandera et al. |

(Continued)

FOREIGN PATENT DOCUMENTS

WO       2014/099170 A1     6/2014

*Primary Examiner* — Reginald R Reyes
(74) *Attorney, Agent, or Firm* — Howard & Howard Attorneys PLLC

(57) ABSTRACT

A system for transmitting information to users via a website or mobile application is described herein. The system includes a database and a server including a processor. The processor is programmed to receive a transmittal request to transmit a communication message to a recipient address, select a recipient type associated with the recipient address, and responsively generate a unique communication identifier including information indicative of the selected recipient type and the communication message. The processor generates and transmits a notification message including the unique communication identifier to the recipient address. The processor also receives a display request to display the communication message in response to a recipient user accessing the unique communication identifier including the selected recipient type. The processor determines promotional information associated with the recipient type and displays the communication message and the associated promotional information to the recipient user via user computing device.

20 Claims, 14 Drawing Sheets

(56) References Cited

U.S. PATENT DOCUMENTS

| | | |
|---|---|---|
| 6,820,058 B2 | 11/2004 | Wood et al. |
| 7,246,070 B2 | 7/2007 | Schwartz et al. |
| 7,613,620 B2 | 11/2009 | Salwan |
| 8,239,215 B2 | 8/2012 | Vovan et al. |
| 8,542,809 B2 | 9/2013 | Bookstaff |
| 8,627,084 B1 | 1/2014 | Pauker et al. |
| 2001/0032124 A1 | 10/2001 | Savage et al. |
| 2002/0184097 A1 | 12/2002 | Hijiri et al. |
| 2004/0260577 A1 | 12/2004 | Dahlin et al. |
| 2005/0201345 A1* | 9/2005 | Williamson ........... G16H 40/63 370/338 |
| 2006/0080146 A1 | 4/2006 | Cook et al. |
| 2006/0190296 A1 | 8/2006 | Hackett et al. |
| 2008/0021739 A1 | 1/2008 | Brock |
| 2010/0030580 A1 | 2/2010 | Salwan |
| 2010/0082367 A1* | 4/2010 | Hains .................. G06F 19/3456 705/2 |
| 2012/0278098 A1 | 11/2012 | Vovan et al. |
| 2014/0180701 A1 | 6/2014 | Grilli et al. |
| 2014/0304505 A1* | 10/2014 | Dawson .............. G06F 21/6227 713/165 |

* cited by examiner

| User ID | Comm. Address | Location ID | Recipient Type |
|---|---|---|---|
| Doctor A | Dr@doc.com | Anytown, USA | Doctor |
| Doctor B | DrB@dentist.com | Othertown, USA | Doctor |
| Patient A | PatA@patient.com | Anytown, USA | Patient |
| Patient B | PatB@patient.com | Anytown, USA | Patient |
| Vendor A | Vend1@vnd.com | Location A | Vendor |
| Vendor B | VendB@vend.com | Location B | Vendor |

FIG. 8

| User ID | Promotional Information |
|---|---|
| Doctor A | Vender X promotions |
| Doctor B | Vendor Y promotions |
| Patient A | Oral Hygiene vendor X promotions |
| Patient B | Vender Y offers |

FIG. 9

| Location ID | Promotional Information |
|---|---|
| Location A | Sponsor A promotion/information |
| Location B | Sponsor B promotion/information |

SYSTEM FOR SECURELY TRANSMITTING MEDICAL RECORDS AND FOR PROVIDING A SPONSORSHIP OPPORTUNITY

CROSS-REFERENCES TO RELATED APPLICATIONS

This application claims priority to U.S. Provisional Patent Application Ser. No. 61/949,656, filed on Mar. 7, 2014, which is hereby incorporated by reference in its entirety for all purposes.

TECHNICAL FIELD

The subject matter disclosed herein relates generally to providing information to a user via a website or mobile application, and more particularly, to systems, methods, and computer-readable storage media that allows users to access data files and view promotional information via a website or mobile application. The systems, methods, and computer-readable storage media provide secure communications over the Internet, and more particularly provide a secure and/or HIPAA compliant method of document exchange between health care service providers, defined here as the vertical initiator, (doctors, a hospital/practice personnel, etc.), service consumers (patients) and third parties (patient representatives, insurance companies personnel, etc.), as well as secure manual and automated communications over the internet between medical insurers and serviced providers and patients.

BACKGROUND OF THE INVENTION

Various parties involved into interactions related to the health care need to exchange documents. Very often it is more efficient to do it when the documents are in electronic form (computer files, records in a database, etc.). However nowadays a large number of these transactions are done in non-secure ways, by means of passing to each other media with non-encrypted files, sending non-encrypted files attached to email, placing non-encrypted files on corporate or even public ftp servers. Such actions violate HIPAA requirements.

There are several known solutions including: For example, files are encrypted on the sender side and sent by email or delivered on a file storing media. Recipient must have a special program to decrypt it. While this works well between often collaborating parties this does not work for interactions between rarely communicating parties (i.e., Doctors and Patients) because they do not spend their efforts to set up safe communication protocols and applications in advance. In addition, there are several methods for online collaboration in the internet. A sender party uploads documents as files to a server where these files are stored. When uploading the document the sender defines a recipient email and the recipient receives email notification with the link to the document. The file is accessible by recipient via the link presented in the notification. Security of these interactions is achieved by: 1.) using secure communication protocols (i.e., SSL) between user side and server side applications; 2.) storing documents on the server as encrypted files; 3.) protecting access to the server by password and/or second factor authentication means; and 4.) automatically deleting a document on the server after preliminary set or configurable expiration period.

These solutions support basic and universal features for simple collaboration over the internet. In many cases desirable collaboration scenarios can be different depending on the specific industry vertical in which the collaboration happens, and the types of the involved users. This is not achievable by the described existing services. This problem is resolved by providing application programming interfaces for integration with an industry specific 3rd party corporate system. In this case user types and appropriate collaboration scenarios are defined in these corporate systems and the service stays industry neutral. This approach, however, can be quite expensive and not applicable for small businesses.

The present invention provides methods to build similarly functioning systems such that they are more adjustable for different industry verticals and different collaboration scenarios. The goal is to make secure online collaboration platforms that are more convenient and attractive to the user.

SUMMARY OF THE INVENTION

In different embodiments of the present invention, systems, methods, and computer-readable storage media allow users to securely transmit information to recipients and to display targeted promotion information based on the type of recipients receiving the information.

In one embodiment, a system for transmitting information to users via a website or mobile application is provided. The system includes a database and a server including a processor. The database includes a plurality of user records and a plurality of promotional records. The user records include recipient addresses and recipient types. The promotional records include promotional information associated with the recipient types. The processor is programmed to receive a transmittal request, from a vertical initiator user, to transmit a communication message to a recipient address, select a recipient type associated with the recipient address, and responsively generate a unique communication identifier including information indicative of the selected recipient type and the communication message. The processor generates and transmits a notification message including the unique communication identifier and to the recipient address. The processor also receives a display request to display the communication message in response to a recipient user accessing the unique communication identifier including the selected recipient type and the communication message associated with the unique communication identifier. The processor determines promotional information associated with the recipient type and displays the communication message and the associated promotional information to the recipient user via the website or mobile application.

In another embodiment, a method for transmitting information to users via a website or mobile application is provided. The method includes receiving, by a processor, a transmittal request, from a vertical initiator user, to transmit a communication message to a recipient address, selecting a recipient type associated with the recipient address, and responsively generate a unique communication identifier including information indicative of the selected recipient type and the communication message. The method includes generating and storing, by the processor, a notification message including the unique communication identifier in a database, and transmitting the notification message to the recipient address. The method also includes receiving a display request to display the communication message in response to a recipient user accessing the unique communication identifier. The display request including the selected recipient type and the communication message associated with the unique communication identifier. The method further includes determining promotional information associated with the recipient type and displaying the communication message and the associated promotional information to the recipient user via the website or mobile application.

In yet another embodiment, one or more non-transitory computer-readable storage media, having computer-executable instructions embodied thereon are provided. When executed by at least one processor, the computer-executable instructions cause the processor to receive a transmittal request, from a vertical initiator user, to transmit a communication message to a recipient address, select a recipient type associated with the recipient address, and responsively generate a unique communication identifier including information indicative of the selected recipient type and the communication message. The processor generates and transmits a notification message including the unique communication identifier and to the recipient address. The processor also receives a display request to display the communication message in response to a recipient user accessing the unique communication identifier including the selected recipient type and the communication message associated with the unique communication identifier. The processor determines promotional information associated with the recipient type and responsively displays the communication message and the associated promotional information via a website or mobile application.

BRIEF DESCRIPTION OF THE DRAWINGS

Non-limiting and non-exhaustive embodiments of the present invention are described with reference to the following figures. Other advantages of the present disclosure will be readily appreciated, as the same becomes better understood by reference to the following detailed description when considered in connection with the accompanying drawings wherein:

FIGS. 8-21 are illustrations of exemplary screenshots from the system of FIG. 1, according to an embodiment of the present invention.

Figure 1:
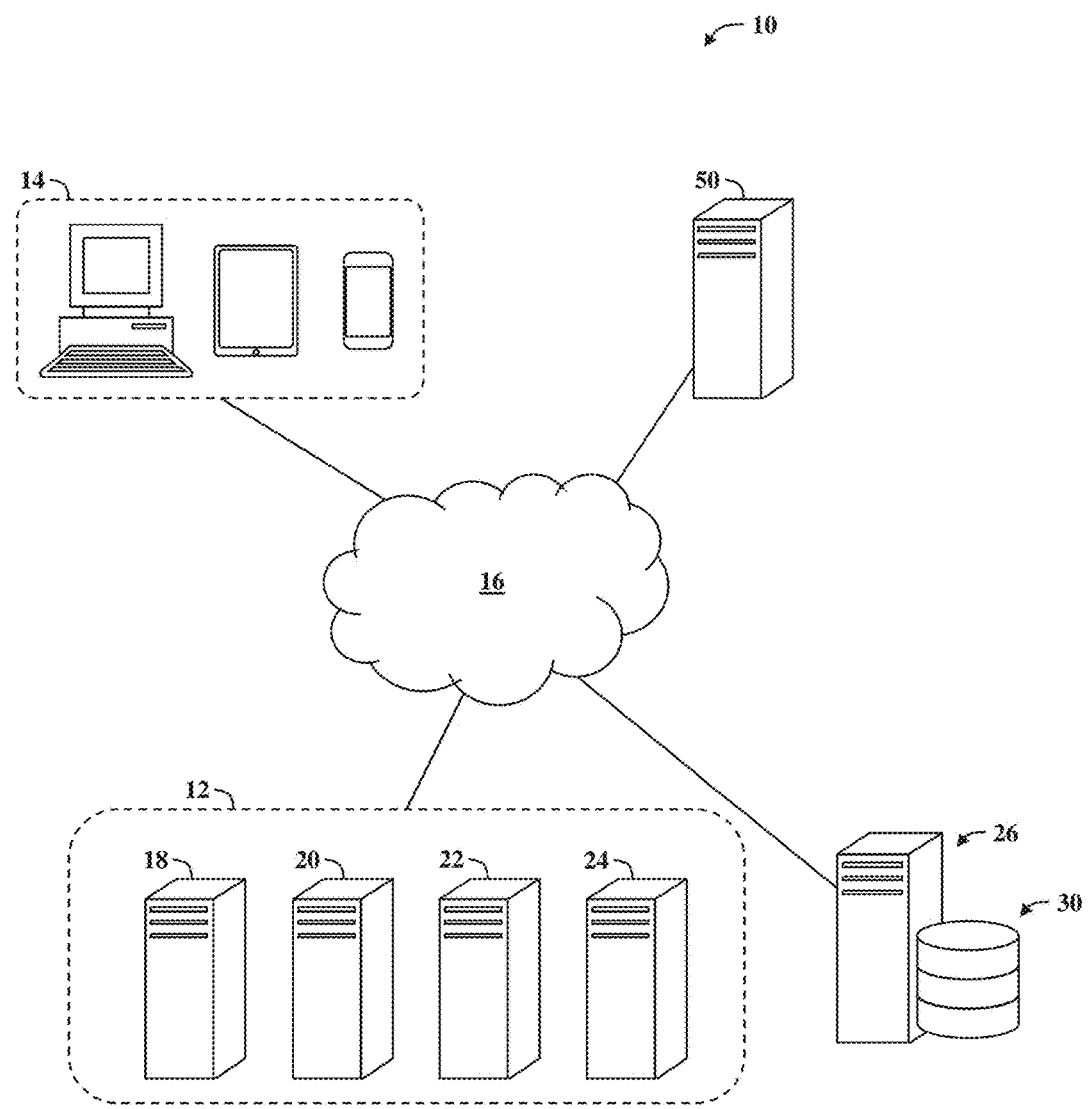
FIG. 1 is a schematic illustrating various aspects of a system, according to the present disclosure.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

DETAILED DESCRIPTION

The disclosure particularly describes how information such as medical records may be transmitted to a user via a website or mobile application and how promotional information may be selected and displayed to the user on the website or mobile application. Particularly, the present disclosure describes a system that is configured to connect buyers to sellers both in a business-to-business (B2B) and business-to-consumer (B2C) environment via marrying: 1) the fundamental buyer need to exchange secure information with its stakeholders (e.g., for the dental industry patients & referring Doctors); and 2) the vendors need to "connect" to specific vertical industry channels including, but not limited to, medical, dental, legal, Real Estate, non-hospital affiliated health professions, and/or any suitable business services.

For example, the system allows users to identify members of vertical channels and allow the members to securely exchange information over the Internet. For example, the system allows a vertical initiator, e.g., a user that belongs to a specific vertical, to: create groups of related users (e.g., Dentist or office manager connecting to patients—one dentist has on average 1500 patients), contact other doctors with different specialties to refer some of their patients (e.g., a General Practitioner contacting an orthodontist), and/or contact other businesses (e.g., accountants, lawyers, real estate agents, labs) possibly initiating another vertical.

The system also allows users to upload electronic data files of any type (e.g., text files, sound files, video files, URLs) such as, for example, document files to the system and send secure messages to a recipient notifying the recipient of the availability of the data files. The system allows the recipient to view and download the data files from a website or mobile application displayed by the system. The system also identifies a recipient type associated with the recipient viewing the data files and selects and displays targeted promotional information to the recipient via the website. In addition, the system may also include location data associated with various users. The system may receive location information associated with the device being used to access the system and allows the corresponding user to access the system upon verification of the location information with the location data.

For example, the system may request a user to enter login information via the website to access the system. Upon receiving the login information, the system may identify a user account associated with the login information including location data associated with the user account. The system may also determine a location of the device being used to access the system based on location information being transmitted by the device, and allow the user to access the system if the received location information matches the location data included in the corresponding user account. In addition, the system may receive location information included with a request to view the data files and verify the received location information with the location data recorded in the system before allowing the recipient to view and download the data files.

For example, in one embodiment, the system allows a vertical initiator user such as, for example, a medical doctor, to upload patient medical records to the system and to send a notification message to a recipient user notifying the recipient of the availability of the records. The system also allows the vertical initiator to identify the recipient user as a patient. The system generates a notification message such as, for example, an email message including a hyperlink to a website that allows the patient to view and download the medical records. Upon receiving a request to view the website generated by the patient accessing the hyperlink, the system identifies the recipient type associated with the request and selects and displays promotional information to the recipient on the website. For example, the system may associate the request with the patient and select and display promotional messages providing information that is targeted to the patient. In addition, the system detects the recipient's activity on the website including, for example, how the recipient interacts and/or accesses the promotional information being displayed on the website, and generates viewer interest values for use in determining the effectiveness of the promotional messages. By allowing the user to identify a recipient type associated with the recipient of the message, the system is able to provide relevant promotional information to the recipient as the recipient accesses the emailed message. In addition, by verifying the location of the recipient prior to allowing the recipient to access stored document files, the system provides a more efficient method of providing secured documents thus improving the functionality of known computing systems by reducing the amount of computing resources required to transmit secured documents to users.

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

Reference throughout this specification to "one embodiment", "an embodiment", "one example" or "an example" means that a particular feature, structure or characteristic described in connection with the embodiment or example is included in at least one embodiment of the present invention. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

Embodiments in accordance with the present invention may be embodied as an apparatus, method, or computer program product. Accordingly, the present invention may take the form of an entirely hardware embodiment, an entirely software embodiment (including firmware, resident software, micro-code, etc.), or an embodiment combining software and hardware aspects that may all generally be referred to herein as a "module" or "system." Furthermore, the present invention may take the form of a computer program product embodied in any tangible media of expression having computer-usable program code embodied in the media.

Any combination of one or more computer-usable or computer-readable media (or medium) may be utilized. For example, a computer-readable media may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present invention may be written in any combination of one or more programming languages.

The flowchart and block diagrams in the flow diagrams illustrate the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions. These computer program instructions may also be stored in a computer-readable media that can direct a computer or other programmable data processing apparatus to function in a particular manner, such that the instructions stored in the computer-readable media produce an article of manufacture including instruction means which implement the function/act specified in the flowchart and/or block diagram block or blocks.

Several (or different) elements discussed below, and/or claimed, are described as being "coupled", "in communication with", or "configured to be in communication with". This terminology is intended to be non-limiting, and where appropriate, be interpreted to include without limitation, wired and wireless communication using any one or a plurality of a suitable protocols, as well as communication methods that are constantly maintained, are made on a periodic basis, and/or made or initiated on an as needed basis. The term "coupled" means any suitable communications link, including but not limited to the Internet, a LAN, a WAN, a cellular network, or any suitable communications link. The communications link may include one or more of a wired and wireless connection and may be always connected, connected on a periodic basis, and/or connected on an as needed basis. In one embodiment, the system 10 may implement two modes of communication: a) non-secure notification; and/or b) secure transmittal/retrieval of protected content.

With reference to the FIGS. and in operation, the present invention provides a system 10, methods and computer product media that facilitates displaying promotional information to a user and to securely transmit information such as, for example, medical records via a website. Referring to FIG. 1, an exemplary environment in which the system 10 operates is illustrated. In the illustrated embodiment, the system 10 is configured to enable a user to access a website with one or more user computing devices to view and download information and to view promotional messages that are selected based on the type of user viewing the information. In general, the system 10 allows a user to upload data files to the system and transmit a notification to a recipient that allows the recipient to view and download the data files via a website. The system 10 also identifies a recipient type associated with the recipient and selects promotional messages based on the recipient type and displays the selected promotional messages on the website when the recipient accesses the website to download the data files.

For clarity in discussing the various functions of the system 10, multiple computers and/or servers are discussed as performing different functions. These different computers (or servers) may, however, be implemented in multiple different ways such as modules within a single computer, as nodes of a computer system, etc. . . . . The functions performed by the system 10 (or nodes or modules) may be centralized or distributed in any suitable manner across the system 10 and its components, regardless of the location of specific hardware. Furthermore, specific components of the system 10 may be referenced using functional terminology in their names. The function terminology is used solely for purposes of naming convention and to distinguish one element from another in the following discussion. Unless otherwise specified, the name of an element conveys no specific functionality to the element or component.

In the illustrated embodiment, the system 10 includes a server system 12 that is coupled in communication with one or more user computing devices 14 via a communications network 16. The server system 12 includes a website hosting server 18, an authentication server 20, a communication server 22, a promotion server 24, a database server 26, and a database 30. The communications network 16 may be any suitable connection, including the Internet, secure hyper text transfer protocol HTTPs, secure file transfer protocol (FTPs and/or sFTP), an Intranet, LAN, a virtual private network (VPN), cellular networks, etc. . . . , and may utilize any suitable or combination of technologies including, but not limited to wired and wireless connections, always on connections, connections made periodically, and connections made as needed.

The user computing device 14 may include any suitable device that enables a user to access and communicate with the system 10 including sending and/or receiving information to and from the system 10 and displaying information received from the system 10 to a user. For example, in one embodiment, the user computing device 14 may include, but is not limited to, a desktop computer, a laptop or notebook computer, a tablet computer, smartphone/tablet computer hybrid, a personal data assistant, a handheld mobile device including a cellular telephone, any handheld networked device, and the like.

The database server 26 includes a memory device that is connected to the database 30 to retrieve and store information contained in the database 30. The database 30 contains information on a variety of matters, such as, for example, web pages associated with one or more websites, user account records, promotional records, data files, email account records, recipient types, location information, promotional information, and/or any suitable information that enables the system 10 to function as described herein. The user account records may include information on a variety of matters such as, for example, account information related to a user, a user name, user password, address, personal identification number, user profile information, user contact information such as email addresses, phone numbers, mailing address, location information such as resident/business address. In addition, the user account records may include corresponding unique user identifiers.

For example, in one embodiment, the unique user identifier may include a combination of a username and password. Alternatively, in another embodiment, the unique user identifier may include a personal identification number, or a random identification number assigned to a corresponding user account. The unique user identifier may also include a mobile device identifier, such as, for example, a cellular phone number and/or wireless internet address. In one embodiment, the system 10 generates and stores a plurality of user account records 32 (shown in FIG. 8) and a plurality of promotional records 34 (shown in FIGS. 9 and 10) in the database 30. Each user account record 32 may include a user ID, a communication address, a location identifier, and/or a recipient type. The communication address may include, but is not limited to, an email, a phone number, and/or any suitable combination of data that enables the system 10 to send and received information to the user. The recipient type includes information that is used to identify the user records with one or more vertical initiators and indicates a relationship between the user and the vertical initiator. One or more promotional records 34 may include promotional information and corresponding recipient types. In addition, in one embodiment, as shown in FIG. 10, one or more promotional records 34 may include a location identifier and promotional information associated with the location identifier.

The website hosting server 18 is configured to host a website 36 that is accessible by a user via one or more user computing devices 14. The website hosting server 18 retrieves and stores web pages 38 (shown in FIGS. 11-21) associated with one or more websites 36 in response to requests received by the user via the user computing device 14 to allow users to interact with the website and access data files stored in the database 30 and view promotional information related to products such as, for example, goods and/or services via the website. In one embodiment, the website hosting server 18 is configured to generate and display web pages 38 associated with the website in response to requests being received from users via corresponding web browsers that are displayed on the user computing devices 14. In one embodiment, the website hosting server 18 may be configured to transmit information to the one or more user computing devices 14 in response to requests received via a mobile application installed and operating on a user computing devices 14. Moreover, the website hosting server 18 may generate and transmit data to the user computing device 14 to display images similar to the website and/or webpages on the user computing device 14 via the mobile application. In one embodiment, the web pages 38 include a plurality of user selection areas 40 that correspond to specific operations that may be initiated by the user. The website hosting server 18 may also detect and monitor user activity associated with the corresponding selection areas 40 and perform specific operations based on received user input.

For example, in one embodiment, the website hosting server 18 may display a login webpage (shown in FIG. 11) in response to receiving user request to access the system 10. The system 10 may receive user information via the login website 36 for use in verifying the information received from the user and allow the user to interact with the system 10 to access and/or store information in the database 30. In addition, the website hosting server 18 may display a communication area 42 that allows a user to upload data files to the system and transmit a communication message to one or more recipients. The website hosting server 18 may also display a promotion area 44 that displays promotional information to the user as the user interacts with the system 10 via the website.

In the illustrated embodiment, the authentication server 20 receives the login information entered via a login area 46 (shown in FIG. 11) displayed with the login webpage and validates the login information and identifies the user account associated with the login information. In addition, the authentication server 20 may also receive location data associated with a location of the user computing device 14 being used to access the system 10 and compare the received location data with location information associated with the identified user record. For example, in one embodiment, the authentication server 20 may receive a request from the vertical initiator via a user computing device 14 to access the system 10 including login information and location data received from the user computing device 14. The authentication server 20 identifies the user account associated with the login information and verifies that the received location data matches the location identifier included in the corresponding user account. If the location data does not match, the authentication server 20 may request additional information be provided by the user such as, for example a response to a security question, and/or send a verification email message to the address included in the user account. Upon receiving the additional information and/or a response to the verification email, the authentication server 20 then allows the user to access the system 10.

Figure 7:
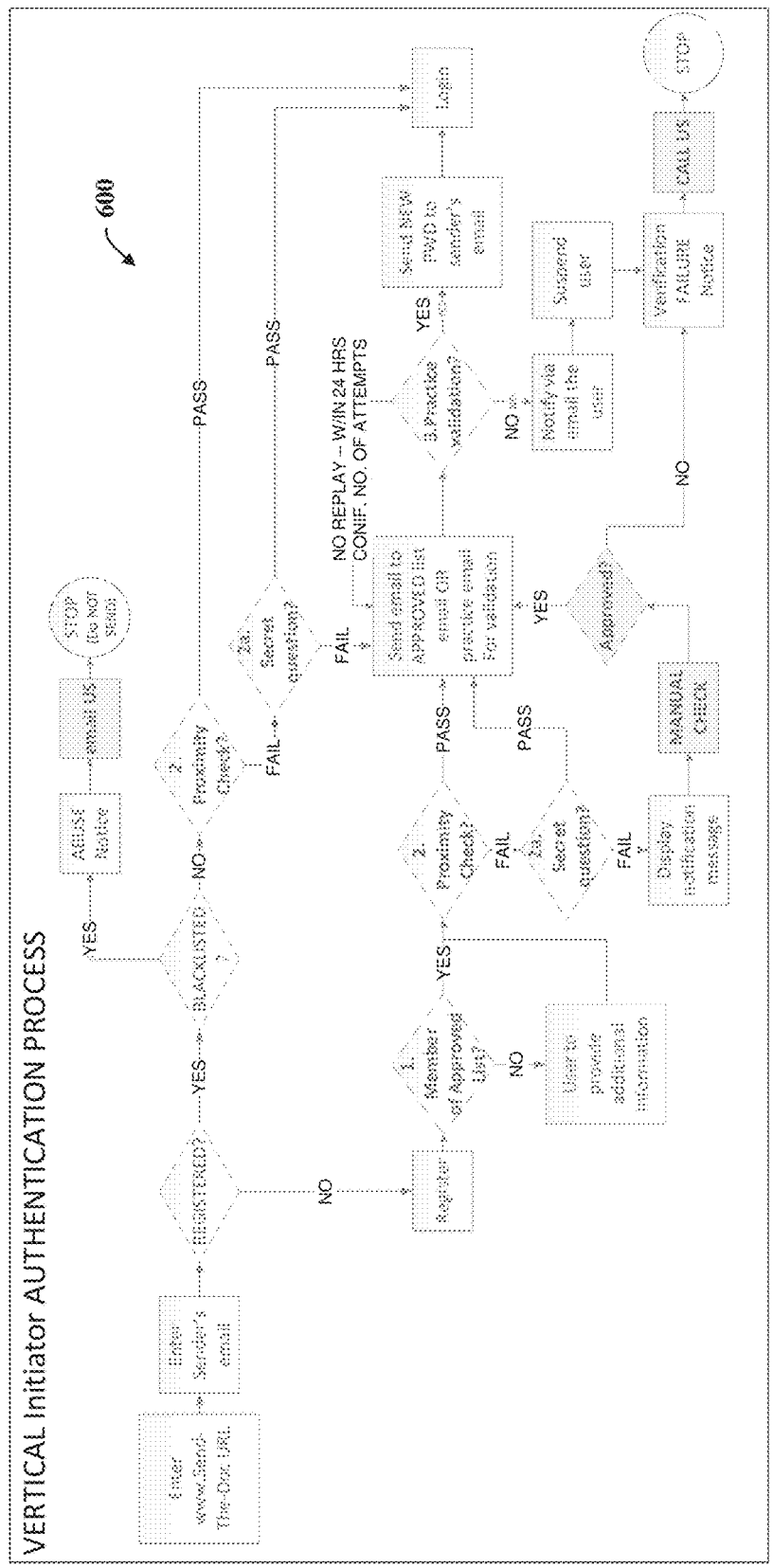

For example, as shown in FIG. 7, the authentication server 20 may conduct an authentication process 600 including displaying the login webpage and receiving a request to access the system 10 via a user communication device 14. The request may include corresponding login information such as, for example a username and password being entered by a corresponding vertical initiator user. The authentication server 20 determines if a user record 32 included in the database 30 includes login information that matches the received login information. If a matching user record is not found in the database 30, the authentication server 20 requests the user to register with the system 10 and displays a user registration page 48 requesting information required to generate a corresponding user account. If the authentication server 20 identifies a matching user account record 32, the authentication server 20 determines if the location information received from the user computing device 14 matches the location data included in the matched user account record 32. If the received location data matches the user account record, the authentication server 20 allows the user to access the system 10. If the location data does not match the user account record, the authentication server 20 sends a verification request to the communication address included in the user account record and/or requires additional information from the user to verify the identity of the vertical initiator user.

The authentication server 20 displays the user registration page 48 to receive information for use in generating a user account record. The information may include, but is not limited to, a user ID, a password, user name, a name of the associated business and/or practice, and a zip code and/or other location identifying information associated with the associated business. Upon receiving the registration information, the authentication server 20 may determine if the associated business and/or user name is included in a predefined list of businesses and/or user names included in the database 30.

In one embodiment, the authentication server 20 may transmit a verification request to a $3^{rd}$ party server 50 to receive information associated with a list of vertical initiator users and/or businesses, and determines if the received registration information matches one or more records included in the received information. If the registration information is not included in the predefined list and/or the information received from the $3^{rd}$ party server 50, the authentication server 20 may request additional information from the user for use in verifying the identity of the user. The authentication server 20 may also determine if the location data received from the user computing device matches location information included in the predefined user list and/or the user list received from the $3^{rd}$ party server. If the location data is not included in the user lists, the authentication server 20 may request additional information from the user.

In addition, if the received location data matches the information included in the user lists, the authentication server 20 may send a verification request to the communication address included in the registration information to allow the user to verify the identity of the vertical initiator user. After verifying the identity of the user, the authentication server 20 may generate a corresponding user account and allow the user to access the system 10.

The communication server 22 is configured to allow users to upload data files to the database 30 and transmit communication messages to recipient users to notify the recipient user that the corresponding data file is accessible to the recipient user. The communication server 22 also allows the recipient user to view and/or download the data files via the website 36. For example, in one embodiment, the communication server 22 may receive a transmittal request, from a vertical initiator user, to transmit a communication message 52 (shown in FIGS. 15-18) to a recipient address via the communication area 42 (shown in FIGS. 11, 13, and 14) displayed with the website 36. The communication server 22 may also allow the user to select a recipient type 54 associated with the recipient address. In addition, the communication server 22 may generate a unique communication identifier 56 (shown in FIG. 17) such as, for example a hyperlink, including information indicative of the selected recipient type and the communication message 52. The communication server 22 may also generate the unique communication identifier 56 including information associated with the vertical initiator user. The communication server 22 also generates and transmits a notification message 58 (shown in FIG. 15-17) including the unique communication identifier 56 and to the recipient address. In one embodiment, the communication server 22 allows the initiator user to select a recipient type associated with the recipient address, and generates and stores a corresponding user record including the recipient address and the user selected recipient type in the database 30. The communication server 22 may also select a recipient type associated with the recipient address entered by the vertical initiator. For example, the communication server 22 may identify a corresponding user account record associated with the recipient address and select the corresponding recipient type included in the identified user account record.

The communication server 22 also allows the user to upload one or more data files to the database 30 via a document upload page 60 (shown in FIG. 14) displayed with the website 36. For example, the communication server 22 may received a transmittal request including a request to transmit at least one data file to the recipient address, receive information indicative of the data file and generate and store a corresponding file record including the received information in the database 30. The communication server 22 may also generate the unique communication identifier 56 including information indicative of the data file. In addition, the communication server 22 may also allow users to cancel previously sent communication messages sent to recipient users. For example, in one embodiment, the communication server 22 may receive a request to cancel the transmission of a previously sent communication and/or notification message and/or receive a request to restrict access to an uploaded data file by a recipient. The communication server 22 may responsively update the corresponding file record to restrict access to the recipient. In addition, the communication server 22 may also transmit a notification message to the corresponding recipient address notifying the recipient of the cancelled message.

In the illustrated embodiment, the communication server 22 also receives a display request to display the communication message 52 in response to the recipient user accessing the unique communication identifier 56 and retrieves and displays the corresponding communication message in response to receiving the display request. For example, the communication server 22 may received a request from a user computing device 14 that is indicative of a recipient user accessing the hyperlink included in an email message transmitted by the communication server 22 to the recipient address. In response to the received request, the communication server 22 may retrieve the communication message 52 via the website 36.

In addition, the communication server 22 may also generate a unique data file identifier 62 (shown in FIG. 18) associated with the previously uploaded data file and display the unique data file identifier with the communication message 52. The communication server 22 may also allow the recipient user to access the unique data file identifier via the corresponding user computing device 14 and responsively retrieve and display and/or transmit the corresponding data file to the user computing device 14.

The communication server 22 may also generate and store communication records 64 (shown in FIGS. 19-21) that include information associated with the transmission and receipt of communication messages initiated by the corresponding user. The communication records 64 allow the user to monitor communication messages that have been sent from, and sent to the corresponding user communication address.

Figure 11:
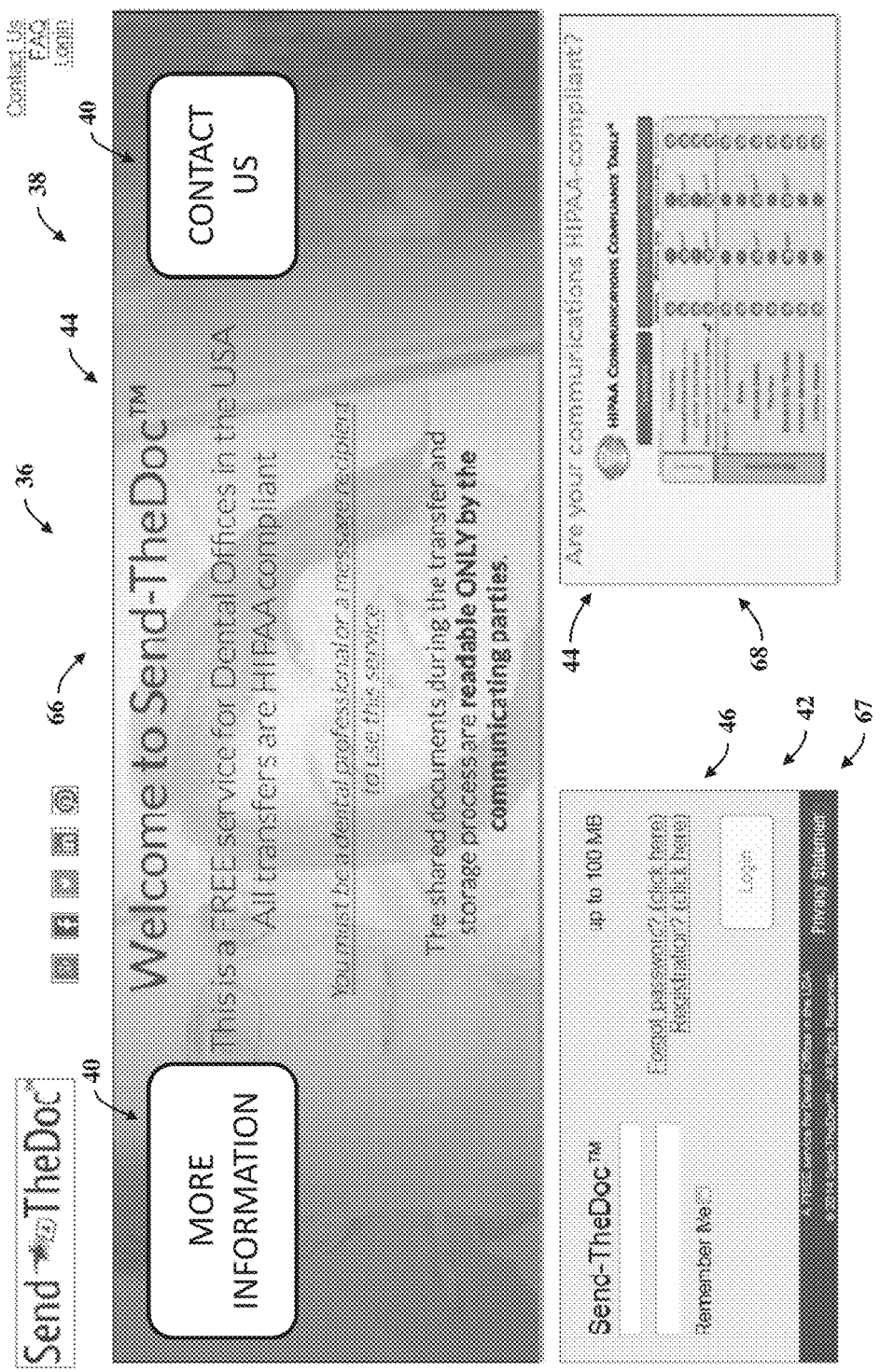
Figure 13:
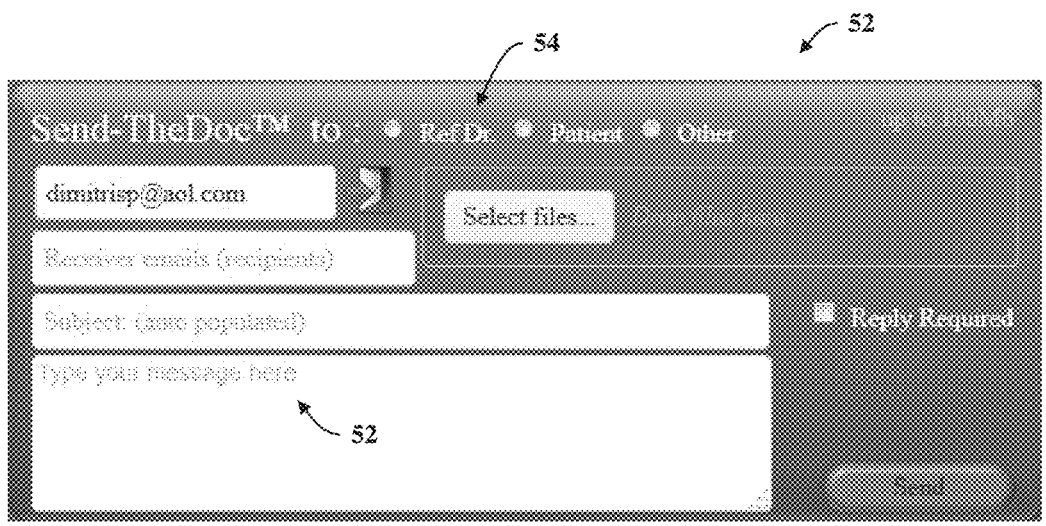
Figure 14:
Figure 15:
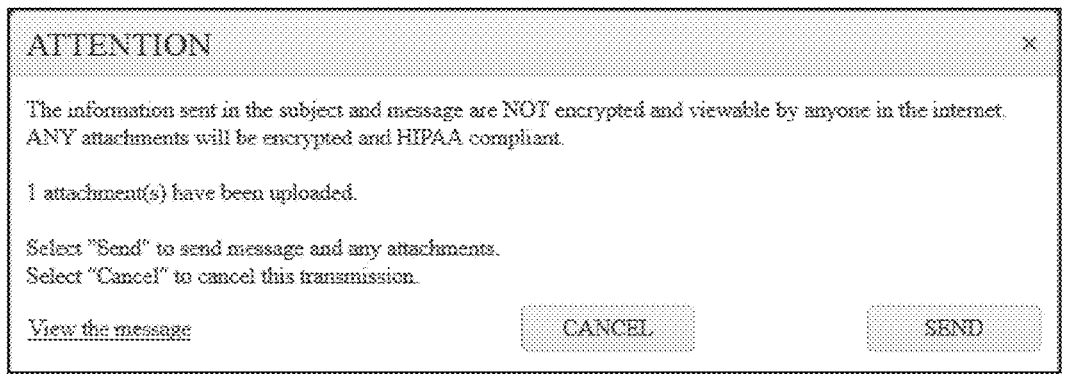
Figure 16:
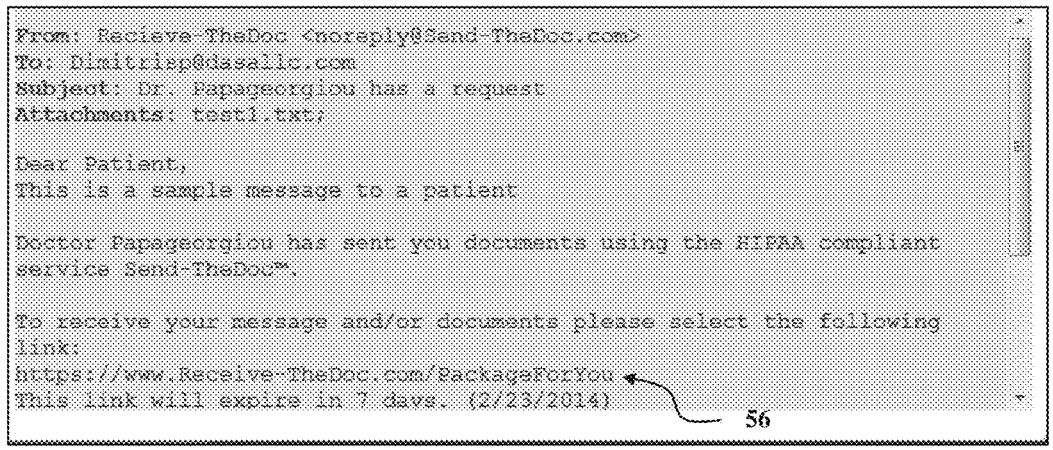
Figure 17:
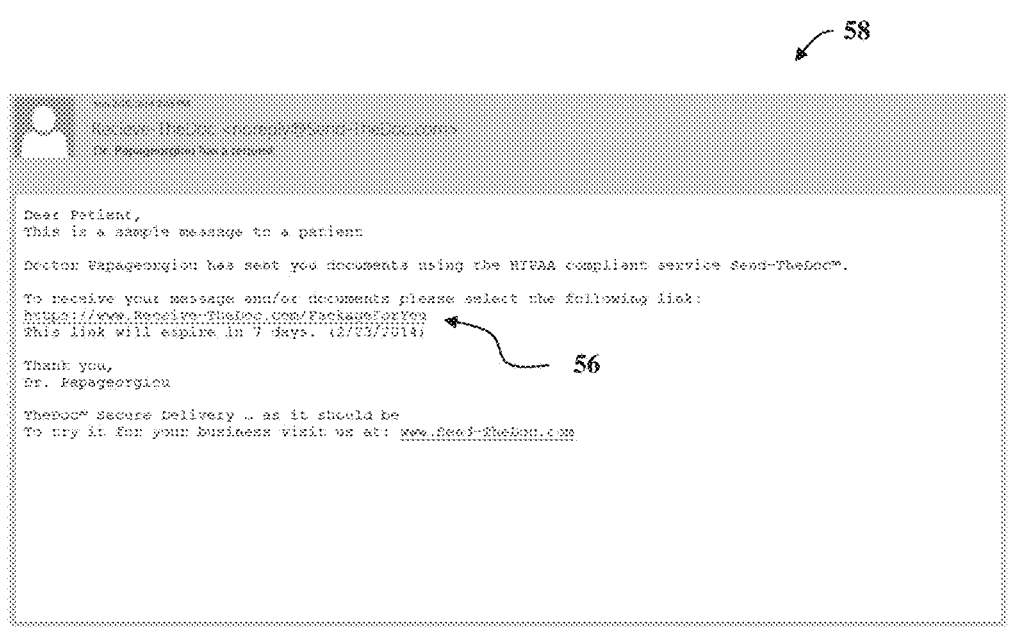
Figure 18:
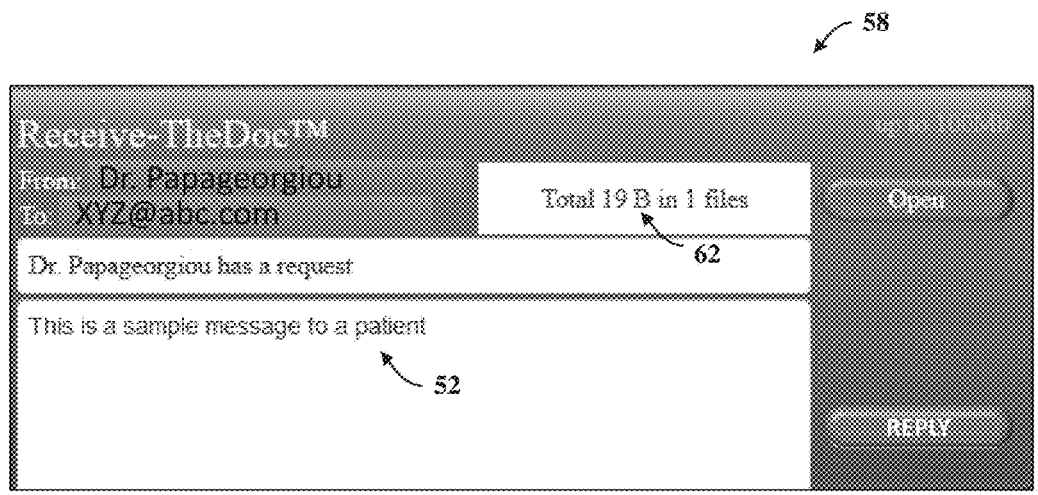

In the illustrated embodiment, the promotion server 24 receives the display request to display the communication message 52 in response to the recipient user accessing the unique communication identifier 56, identifies the recipient type associated with the display request, and determines promotional information associated with the recipient type 54. For example, in one embodiment, the promotion server 24 identifies the recipient type, retrieves the promotion record 34 associated with the recipient type, determines the promotional information included in the promotion record, and displays the promotion information to the recipient via the website 36. In addition, the promotion server 24 may also identify the promotion record associated with location data received from the corresponding user computing device 14 and determine and display the promotional information associated with the location data. For example, as shown in FIG. 11, the promotion server 24 may display location-based promotional information in a regional area 66 of the webpage 38, and display recipient type-based promotional information in a recipient area 68 of the webpage 38. By retrieving information that is generated based on the recipient type and the location of the user, the promotional information displays more relevant information to the user.

In the illustrated embodiment, the promotion server 24 displays the promotion areas 44 including one or more user selection areas 40 and detects and monitors user activity associated with a user accessing the information displayed in the corresponding areas. The promotion server 24 may also generate and store viewer interest values associated with the user activity. The viewer interest values may be used to determine how long a user views a specific advertisement and/or promotional information, click-through statistics, whether the user requests additional information, and/or a number of views received from a particular advertisement. For example, in one embodiment, the promotion server 24 may detect recipient activity associated with the displayed promotional information and determine a viewer interest value indicative of the associated recipient activity value.

Figure 2:
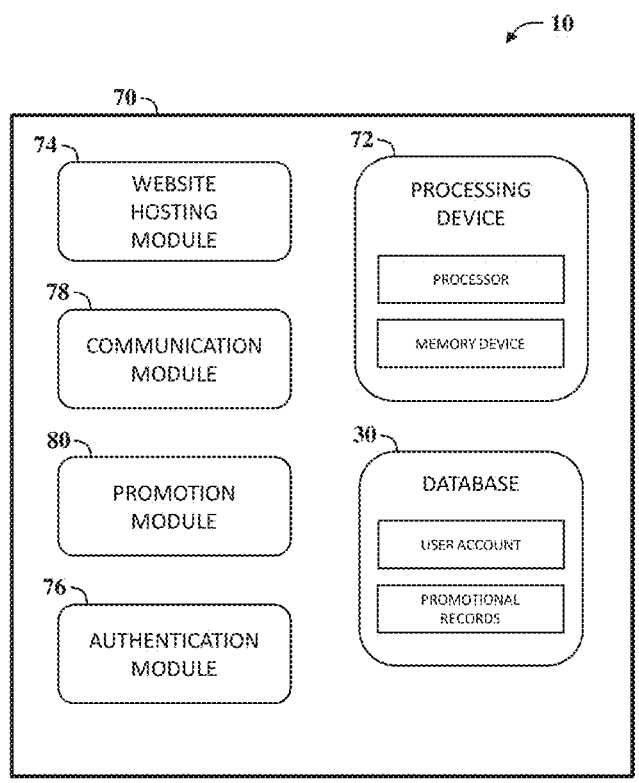
FIG. 2 is a schematic illustrating example components of a server, according to an embodiment of the present invention.

Referring to FIG. 2, in one embodiment, the system 10 may include a system server 70 that is configured to perform the functions of the website hosting server 18, the authentication server 20, the communication server 22, the promotion server 24, and the database server 26. In the illustrated embodiment, the system server 70 includes a processing device 72 and the database 30.

The processing device 72 executes various programs, and thereby controls components of the system server 70 according to user instructions received from the user computing device 14. The processing device 72 may include memory, e.g., read only memory (ROM) and random access memory (RAM), storing processor-executable instructions and one or more processors that execute the processor-executable instructions. In embodiments where the processing device 72 includes two or more processors, the processors can operate in a parallel or distributed manner. In an example, the processing device 72 may execute a website/application hosting module 74, an authentication module 76, a communications module 78, and a promotion module 80.

The processing device 72 may also include a memory device for storing programs and information in the database 30, and retrieving information from the database 30 that is used by the processor to perform various functions described herein. The memory device may include, but is not limited to, a hard disc drive, an optical disc drive, and/or a flash memory drive. Further, the memory device may be distributed and located at multiple locations.

The website/application hosting module 74 may be programmed to perform some or all of the functions of the website hosting server 18 including hosting various web pages associated with one or more websites that are stored in the database 30 and that are accessible to the user via the user computing device 14. The website/application hosting module 74 may be programmed to generate and display web pages associated with a website in response to requests being received from users via corresponding web browsers.

The authentication module 76 may be programmed to perform some or all of the functions of the authentication server 20 including verifying the identity and location of users accessing the system. In addition, the authentication module 76 may be configured to conduct the authentication process 600 shown in FIG. 7.

The communications module 78 may be programmed to perform some or all of the functions of the communication server 22 including retrieving various data and information from the database 30 and sending information to the user computing device 14 via the communications network 16 to enable the user to access and interact with the system 10. In one embodiment, the communications module 78 displays various images on a graphical interface of the user computing device 14 preferably by using computer graphics and image data stored in the database 30 including, but not limited to, web pages, product records, sorted groups, product lists, and/or any suitable information and/or images that enable the system 10 to function as described herein. The communications module 78 may also be configured to generate and transmit notification messages including unique communication identifiers, receive display requests to display the communication messages, and display the communication messages including allowing users retrieve and display data files included in the database 30.

The promotion module 80 may be programmed to perform some or all of the functions of the promotion server 24 including identifying and displaying promotional information on the website 36 as a function of identified recipient types and/or location data. The promotion module 80 may also determine viewer interest values associated with the displayed promotional information based on user activity on the website 36.

FIGS. 3-7 are flowcharts of methods 200, 300, 400, 500, and 600 that may be used with the system 10 for displaying information on a website. The methods include a plurality of steps. Each method step may be performed independently of, or in combination with, other method steps. Portions of the methods may be performed by any one of, or any combination of, the components of the system 10. FIGS. 8-21 are exemplary graphical displays that may be displayed by the system 10.

Figure 3:
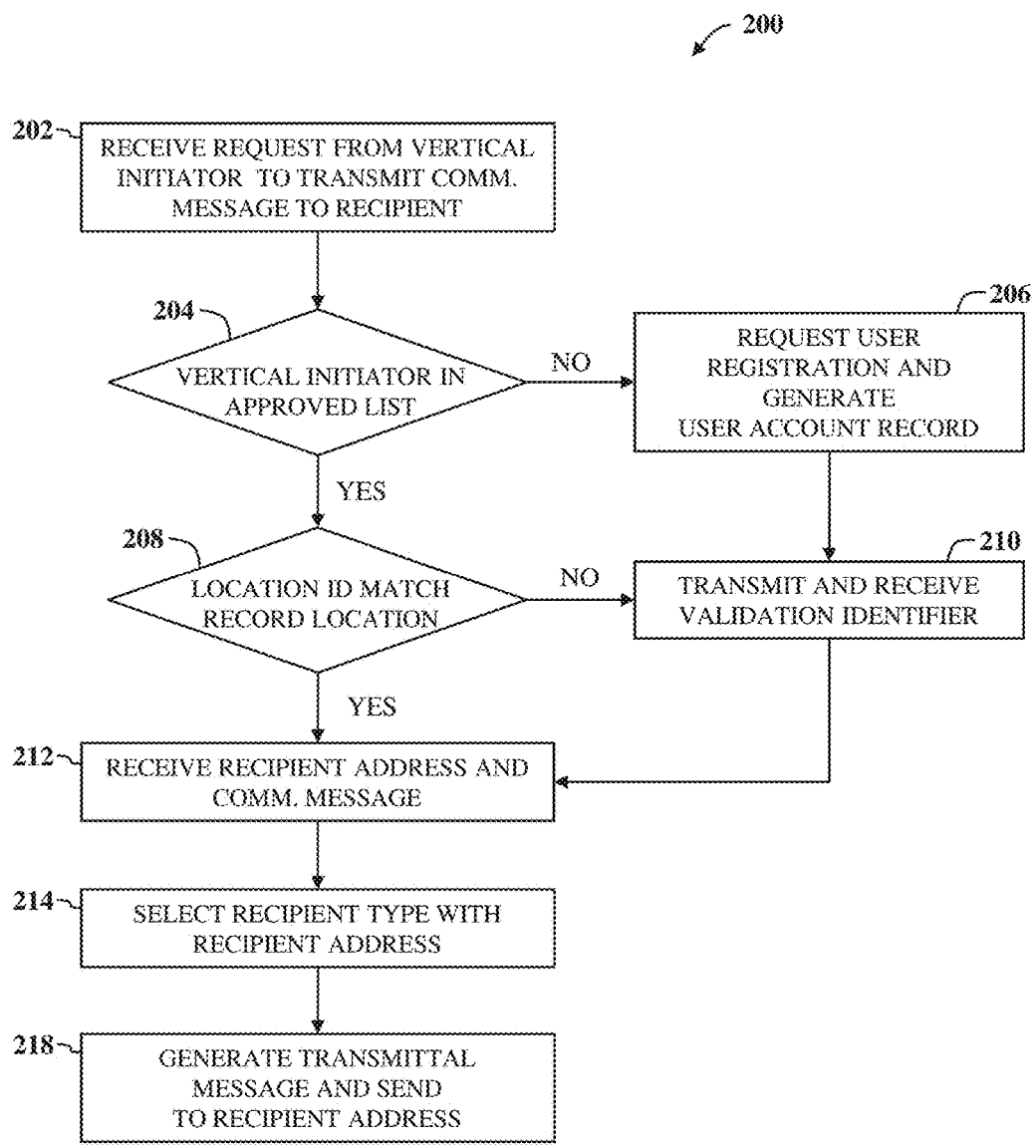
FIGS. 3-7 are flowchart of methods that may be used with the system shown in FIG. 1, according to an embodiment of the present invention.

Referring to FIG. 3, in the illustrated embodiment, in method step 202, the website hosting server 18 receives a request from one or more user computing devices 14 to display one or more web pages 38 associated with a website hosted by the system 10, and retrieves and displays the requested web pages 38 on a corresponding user computing device 14. In one embodiment, the website may include a file-sharing website that enables user to access data files stored on the system 10 via the website. In other embodiments, the website may be a search engine website, an informational website, a blog, a company website, a forum website, a e-commerce website, a social-networking website, and/or any suitable type of website that may be accessed by a user.

In method step 202, the communication server 22 receives a request from a vertical initiator user to transmit a communication message to a recipient, and responsively displays a login webpage. The communication server 22 also receives location data associated with the user communication device 14 being used by the vertical initiator user to access the system 10.

In method step 204, the authentication server 20 conducts the authentication process shown in FIG. 7, and receives login information provided by the vertical initiator user via a corresponding user computing device 14 and determines if the vertical initiator user is included in a predefined approved user account list and/or included the user account records stored in the database 30. If the vertical initiator user is not included in the predefined list and/or the user account records, the authentication server 20 proceeds to method step 206, and displays the registration page to received registration information from the user. If the vertical initiator user is included in the predefined list and/or the user account records, the authentication server 20 proceeds to method step 208. For example, in one embodiment, the authentication server 20 may receive a list of initiator users from a 3rd party server in response to transmitting a verification request to the 3rd party server, and determine if the initiator user is included in a list of initiator users and responsively allow the user to access the system 10

In method step 206, the authentication server 20 displays the registration page 48, receives registration information associated with the vertical initiator user, and proceeds through the authentication process 600 to generate a corresponding user account record.

In method step 208, the authentication server 20 identifies the user account record associated with the login information and determines if the received location data matches the location information included in the user account record 32. If the location data matches the user account record, the system 10 proceeds to method step 212 and allows the user to input a recipient address and communication message. If the location data does not match, the system 10 proceeds to method step 210 and requests addition identification information from the user. For example, in one embodiment, the authentication server 20 may receive the transmittal request including a location identifier associated with the vertical initiator user, determine if the received location identifier matches a location information included in a corresponding user record associated with the vertical initiator user, and responsively allow the user to access the system 10.

In method step 212, the communication server 22 displays the communication area 42 on the website 36 and receives a recipient address and a communication message from the vertical initiator user. In addition, communication server 22 may also allow the user to upload data files being transmitted to the corresponding recipient address.

In method step 214, the communication server 22 selects a recipient type associated with the recipient address. In one embodiment, the communication server 22 may display a plurality of recipient types on the webpage and allows the user to select the recipient type associated with the recipient address. For example, the communication server 22 may allow the initiator user to select a recipient type associated with the recipient address, and responsively generate and store a corresponding user record including the recipient address and the user selected recipient type. In addition, the communication server 22 may also determine a location identified based on the location associated with the vertical initiator user and modify the user record associated with the recipient address to include the location identifier. For example, in one embodiment, the communication server 22 may generate the recipient record including location information included in the corresponding vertical initiator user account. In another embodiment, the communication server 22 may identify a recipient record associated with the recipient address, and select the recipient type included in the identified recipient record.

In method step 218, the communication server 22 generate a unique communication identifier 56 including information indicative of the selected recipient type and the communication message, and generates and transmits a notification message including the unique communication identifier and to the recipient address. In one embodiment, the communication server 22 may generate the unique communication identifier including information associated with the vertical initiator user such as, for example, a corresponding user account record, user address, and/or location information included in the account record. In addition, the communication server 22 may receive the transmittal request including a request to transmit at least one data file to the recipient address, receive information indicative of the data file and generate and store a corresponding file record including the received information, and generate the unique communication identifier including information indicative of the data file.

In one embodiment, the system 10 may receive the transmittal request including a location identifier associated with the vertical initiator user, determine if the received location identifier matches a location information included in a corresponding user record associated with the vertical initiator user, and responsively generate and transmit the transmittal message. In addition, the system 10 may display a verification request to the vertical initiator user upon determining the received location identifier is different than the location information included in the corresponding user record. The system 10 may also receive a validation identifier in response to the verification request, and generate and transmit the transmittal message if the received validation identifier matches a validation identifier included in a user record associated with the vertical initiator.

Figure 4:
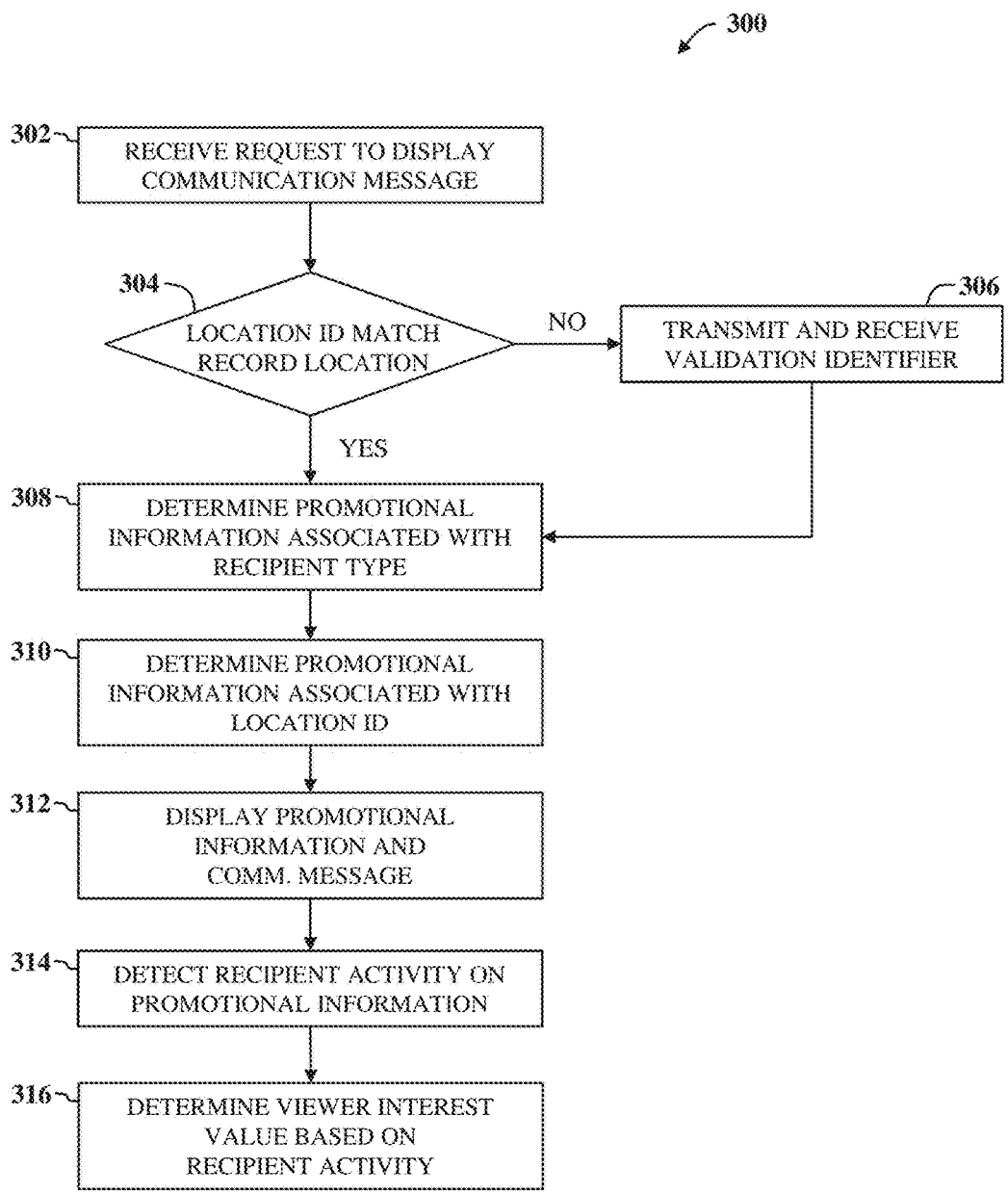
Figure 5:
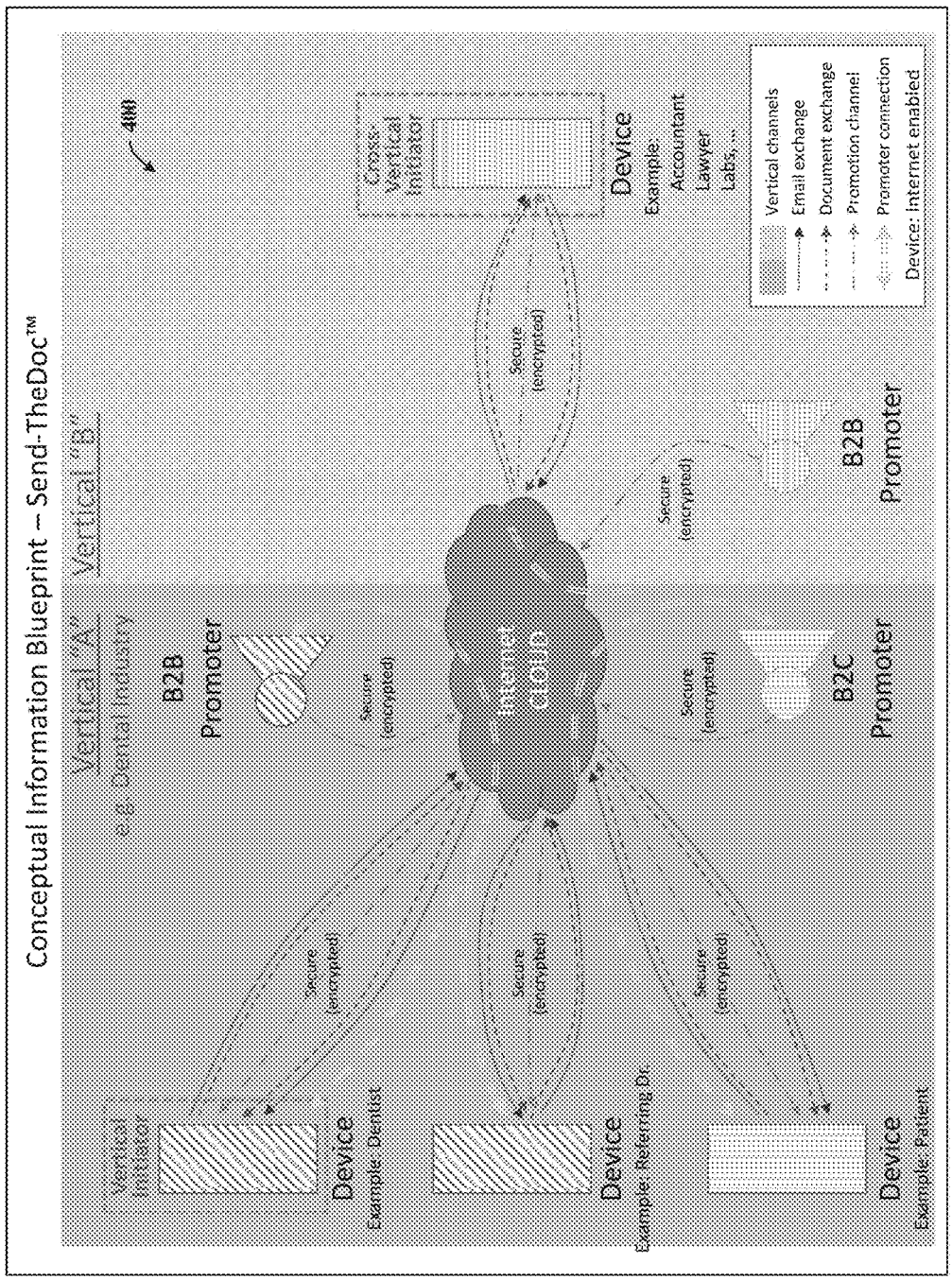
Figure 6:
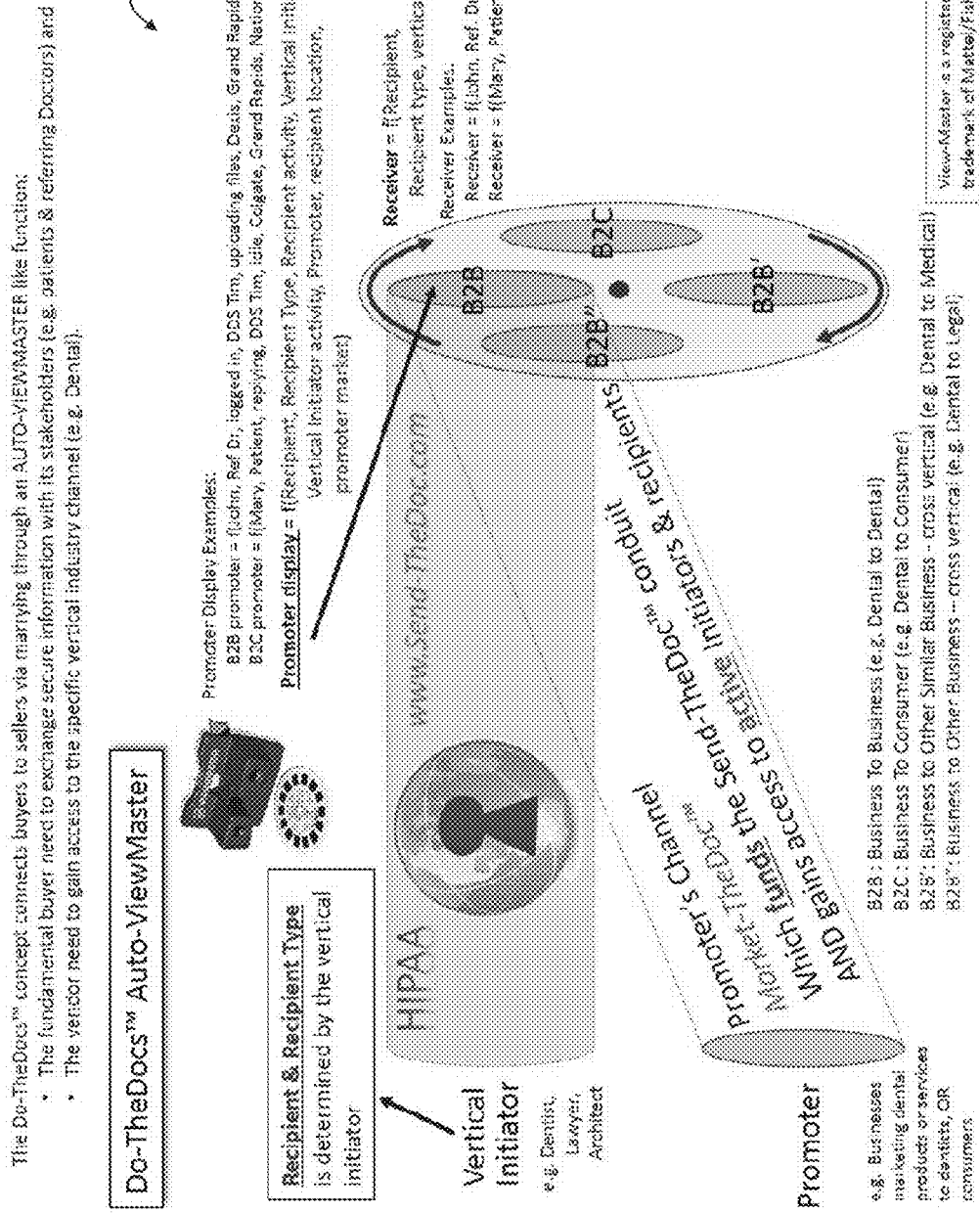

Referring to FIG. 4, in the illustrated embodiment, in method step 302, the communication server 22 receives a request to display the communication message. For example, in one embodiment, the communication server 22 receives a display request to display the communication message in response to a recipient user accessing the unique communication identifier via a corresponding user computing device 14. The display request may also include a corresponding recipient type and the communication message associated with the unique communication identifier.

In method step 304, the communication server 22 receives a location identifier associated with the recipient user and determines if the location identifier matches location information associated with the recipient address. For example, in one embodiment, the communication server 22 may identify a user record associated with the recipient address and display the communication message if the location identifier matches the location information associated with the corresponding recipient address. If the location identifier matches the location information, the system 10 proceeds to method step 308 to determine promotional information to be displayed with the communication message. If the location identifier does not match the location information associated with the recipient address, the communication server 22 may proceed to method step 306 and transmit a validation identifier to the recipient address to verify the identity of the recipient user. For example, in one embodiment, the communication server 22 may send a verification email to the recipient address and receive a validation identifier before displaying the communication message.

In method step 308, the promotion server 24 identifies the recipient type associated with the display request and determines and selects the promotional information associated with the recipient type. For example, in one embodiment, the promotion server 24 identifies a promotion record associated with the recipient type 54 and selects the promotion information included in the identified record.

In method step 310, the promotion server 24 identifies the location identifier included in the display request and associated with the recipient user, and selects and displays promotional information as a function of the associated location identifier. For example, in one embodiment, the promotion server 24 receives the location identifier from the corresponding user computing device 14 being used by the recipient user, and identities and selects the promotion record associated with the location identifier. In addition, the promotion server 24 may receive information associated with the generating vertical initiator and determine promotional information associated with the vertical initiator user in response to receiving the display request.

In method step 312, the communication server 22 receives the promotion information from the promotion server 24 and displays the communication message and the promotion information to the recipient user via the website 36.

In method step 314, the communication server 22 detects and monitors the recipient activity associated with the displayed promotional information.

In method step 316, the communication server 22 generates a viewer interest value indicative of the associated recipient activity value and displays the generated viewer interest values to system users to illustrate the effectiveness of the promotional information being displayed on the website 36.

In one embodiment, the system 10 enables a vertical initiator to transmit information to other users associated with the vertical initiator business vertical chain. For example, in one embodiment, the vertical initiator is a user that belongs to a specific vertical and serves three roles: 1) creates the starburst of users (e.g., Dentist or office manager connecting to patients—one dentist has on average 1500 patients); 2) contacts other doctors with different specialties to refer some of their patients (e.g., a General Practitioner contacting an orthodontist); and 3) contacts other businesses (e.g., accountants, lawyers, real estate agents, labs) possibly initiating another vertical (Picture #1-3).

The system 10 ensures that registered users are members of the vertical channel. There are three nested security mechanisms that secure the user affinity to a specific vertical: 1) reconciliation of user profile to predefined approved list (See FIG. 7); 2) reconciliation of the user profile (e.g., dental practice & zip code) to the location from which the user initiated the internet activity—proximity check, failure of the proximity check will trigger a secret question validation; and 3) Validate new user account via email to the listed practice—practice validation. Special consideration will be given to service providers of the vertical initiator (e.g., Dental consultants, information technology technicians) by using the secret question validation path.

The system 10 may also identify the proper promotion channel. The "recipient types" are introduced and shown in the same window where the sender defines a recipient address/name (shown in FIG. 13). Recipient type names and number of different types that are available for the sender depending on the industry and the sender role in his/her company. A sender can interact with some of the recipient types more often than others. The ease of accessing recipient types depends on the sender probability of using that specific recipient. This probability can be defined in several ways: Recipient types with higher probability of use are shown to the sender and available for quick selection (i.e., Patient and Referral Doctor can be chosen by clicking on a radio button). Less frequently used recipient types are not shown and available for selection through additional action (i.e., shown on a list that is opened when user clicks on a button).

In addition, if the probability of sending a document to a user type by a certain sender role is more than a manually or automatically adjustable value (e.g., 70%) this user type is selected by default, but this should not prevent the sender from selecting another recipient type. Recipient name/address and type are saved in the server, so when this recipient is selected the next time this type is defined automatically. Sender can change the recipient type before and after sending the documents.

System behavior and text in the notification messages addressed to the recipient depend on the selected recipient type. The identification of the recipient type assists in the determination of what promotions will be shown to what user. (e.g., X-Ray equipment to the Front desk and dental hygiene products for the patient).

The system 10 is also configured to address internationalization. For example, in one embodiment, language may be user configurable by means of the user interface. Text: the system 10 is capable of single and double byte characters, user instructions, hover over hints, frequently Asked Questions (FAQs), help files, user interface, service notifications, and promotional information. Voice: the system 10 may provide user instructional videos (responsibility of the service), user speech recognition—configurable by locale, promotional videos (responsibility of the business promoter), In addition, locale vocabulary is configurable by locale and user configurable. Time zones may be displayed relative to GMT and displaying the local time. Currency may be configured by locale. Date formatting—DD-MMM-YYYY (e.g., 1 Feb. 2014) is user configurable defaults by locale, and number formatting is user configurable defaults by locale.

The system 10 also displays a user interface (shown in FIGS. 11-21) that is optimized and configurable. The user interface is optimized to allow the user to complete document sharing process activities and at the same time allow adequate space for the promoters to display their information. The Send-TheDoc graphical user interface indicates how the location of the Send-The Doc user interface can possibly be configured by the user in terms of floating the window, positioning the window as a new default and/or personalizing the Send-TheDoc graphical user interface (e.g., logo, service name). The Send-TheDoc graphical user interface occupies 10% to 28% of the entire display depending and auto-configurable on the vertical and the device (e.g., mobile phone, tablet).

The system 10 also allows the vertical initiator to register and send documents. For example, in one embodiment, the user opens a browser and enter the specified URL (e.g., www.Dental.Send-TheDoc.com). The Send-TheDoc user interface will immediately ask the vertical initiator to enter their email. Once the email is entered the system determines if this is a new or existing user. (shown in FIG. 12)

If the user is a new user: the user interface (shown in FIG. 12) prompts the user to enter user profile information (e.g., email, first, last name, title, practice name, practice email, practice zip code). After the profile registration, the user MUST agree to the end-user-license-agreement and the Business Associate Agreement (for verticals that require HIPAA compliance).

If the user is an existing user: the user is prompted to identify who will be receiving the documents (Dr, patient, other) and then the user enters the email of the recipient and then selects the files to be uploaded. Subsequently the user can edit the auto-generated email subject and message and then defines if a reply is requested (yes or no). At this point the user can select "Send" to send the email and the secure documents (shown in FIGS. 13 and 14). A confirmation message prompts the user one last time before the submission is completed (shown in FIG. 15). The auto-generated messages (shown in FIG. 16) have two parts: Editable—this section can be customized by the vertical initiator to accommodate the specific communication needs; and Non-Editable—this part does not allow editing to guarantee that the receiver link or any other critical service information will not inadvertently be changed.

The system 10 also displays progress indicators for vertical initiator. For example, as the user is adding files, an indicator will prompt the user how much space is left for that specific transmission. When the user uploads files there is an indicator showing the progress of the specific upload. There is an indicator that shows the use how much volume is still available for the month. The user can hover over this indicator and receive a quick report on transmission statistics (i.e., number of files sent this month, number of distinct email users) that can be exported, emailed or printed so that it can be communicated to the office administration. Once the "SEND" button is selected an indicator displays that completion of the submission. Once the vertical initiator selects the "Send" button a window with the final verification shows the vertical initiator what will be received and the user provides the final approval to go ahead and send the email and secure documents (shown in FIG. 15).

The system 10 may also display information to the vertical initiator. For example, the system 10 may display informational and user areas on the user interface screen (shown in FIG. 11). The-UserPad 67: area of the display in which the User fills in the required recipient information and adds ePHI for transmittal to recipient. The-VendorPad 66: area of the display in which the vertical industry vendors promotions are shown. The-InfoPad 68: messaging area of the display in which Service information is displayed for immediate communication with the User. For professional recipients: Service self-promotions, hints and upcoming releases &fixes; information-only vertical industry vendor displays (e.g., website, upcoming events, etc.).

For patient and consumer recipients: Service requests and notifications, informational and educational promotions from Sender. Social Media & Service Invitation area: links to pertinent Service social media sites, utility for User to send an invitation to other professionals to join the Service. Promotion of products specific to the vertical industry (e.g., surgical equipment, X-Ray equipment, dental office services, etc. . . . ). Educational materials to assist dental practice staff to continuously update their knowledge with latest processes/techniques and technologies. (e.g., CE credit services, new ways to periodontal probing, streaming videos from educational institutions, access to electronic magazines, etc. . . . ). Benchmarks/comparisons/performance metrics of similar products or services (e.g., comparison of product technical specifications or services, best-in-class product benchmarks, dental industry performance metrics).

The system 10 also provides promoter accessibility by the vertical initiator via the following means: Indicate product/service interest for the information displayed by selecting: to download &view product/service specifications; to view the vendor website; a "Sponsors" link to indicate interest of finding who is sponsoring the Do-TheDocs™ service; to bookmark the current displayed vendor promotion; to scroll back to find information displayed earlier during the day; to select "Share" so that they can share the current link with other professionals via email; allow selection of social media connections (e.g., like for facebook); complete vendor product/service surveys; case studies/white papers; and allow for web-based searches for subjects in: Send-TheDoc promoters and the ability to sort results: alphabetically, by time slot proximity, by highest interest, by promotion investment level, and over the open internet. In addition, user may select a "notify me" option that allows users to receive information relating to new product updates, new educational material, promotions, press releases, and/or product recalls.

The system 10 also allows users to indicate purchasing interest by selecting: the "Contact us" link to contact the vendor; the "Contact me" link to provide contact information so that the vendor can contact the vertical initiator via email, txt or voice; and/or the "Chat" link to initiate a chat with the vendor that is currently being displayed.

The system 10 may also associate the vertical initiator behavior to the vendor promotion via a unique displayed promotion code to enable analytics that will assist the specific vendor in determining promotion effectiveness, overall product interest and subsequently define an indicator for sales forecast.

The system 10 also allows a vertical initiator receive the replies from users that received documents and "Reply was required". For example, the system 10 may allow the vertical initiator receives an email with the reply from the recipient. Then the vertical initiator selects the link and opens a browser with a Receive-TheDoc interface that enables the vertical initiator to download the secure documents sent (shown in FIGS. 17 and 18). The system 10 may also allows the vertical initiator to use the Send-TheDoc website. The system 10 may generate and display a task manager (shown in FIG. 19) that has a notification bubble that alerts the vertical initiator when there are new messages (similar to MS outlook); then the user can select "Console to go and see all the inbound and outbound traffic". In the inbound traffic the vertical initiator can select the link for any specific recipient to open the submitted message and documents.

In addition, the system 10 may also allow a vertical initiator to manage all the document submissions and required replies. For example, from the www.Send-TheDoc.com menu the vertical initiator can open the console interface and they can see all the users that sent messages. To view and download the messages the vertical initiator can click on the individual message and download the sent files. The inbox, sent and pending lists consist of rows and columns. All columns may be sorted and/or filtered to enable the vertical initiator to find items in an expedited manner (shown in FIG. 20). Once the vertical initiator sends documents to multiple recipients and most of the sent messages require a reply, it becomes challenging to find out who replied and who needs to be reminded. Send-TheDoc console enables the vertical initiator to access "pending reply" messages and remind all recipients or one at a time that their reply is pending. This innovation will save a lot of time and reduce the stress of the operator. The vertical initiator at their own choice they can elect to delete one or all pending items (shown in FIG. 21).

The system 10 may also allow the vertical initiator to broadcast promotions, educational information or general information to their receivers. For example, the vertical initiator can define a broadcast in the following ways: link to the vertical initiator website, standard picture with configurable text, select a picture from a library and configure the text, and/or upload a custom picture or html page. This broadcast will be shown to the receiver as soon as the receiver clicks on the email link that was received and when the Receive-TheDoc website is displayed. The broadcast will be for a limited time (e.g., 1 minute as configured by the service provider or vertical initiator). The broadcast from the vertical initiator may be share display space with business-to-consumer broadcasts and it may also be sequenced (e.g., the vertical initiator broadcast consumes the entire webpage for several seconds and then it consumes a smaller area and the business-to-consumer broadcast takes most of the webpage display space).

The system 10 may also initiate a user filtering process to account for satellite users in a multi-office setting where the operator is working in several offices. For example, the satellite user may be user that serves several vertical initiator locations, whether it is one or multiple corporate entities (e.g., an information technology provider, a roaming hygienist, a part-time assistant or specialist). An authentication of the proximity check may be done using one of the following ways: authentication of a secret phrase which was predetermined by the user during registration; authentication via a separate device (e.g., cell phone or texting device) where the user has to provide the cell phone number associated with the user during registration; and/or a combination of both.

The system 10 also allows the vertical initiator to communicate in a secure way with their customers. For example, the vertical initiator may initiate a "Secure Chat" session with the receiver (e.g., their patient) or referring doctors during business hours. This will ensure that the vertical initiator will be able to securely converse with its receivers instead of using texting which is not HIPAA compliant. The technology utilized to exchange secure chat is the same technology used for the encrypted document delivery. The vertical initiator may also include a "Secure Note" during the document sending process. The secure note is encrypted and visible only from the sender or the receiver with access to Send-TheDoc or Receive-TheDoc.

In addition, the system 10 may also allow the vertical initiator ensure that the transmittal is being opened/read by the correct Recipient (i.e., Additional Security Considerations). It is the responsibility of the vertical initiator to determine the accuracy of the name/email information to be used with the Service. The vertical initiator may initiate e.g., "Send-Receive/Reply cycle" (or any other communications route/cycle as described, herein) based on the following: Requiring that the recipient use a shared password or code which is known to both the Sender and Receiver (e.g., last four digits of the recipient SSN, recipient birth year, etc.). Not requiring the recipient use a shared password or code. This requirement is configurable for the vertical initiator in the Send-TheDoc administrative console.

The system 10 also allows the vertical initiator to automatically transmit multiple and varied ePHI to multiple recipients. For example, the system 10 may include an incremental and a batch mode. Users may send multiple transmissions to multiples of recipients in a single batch operation, or the User may send in a single recipient mode. Sender Email address, fixed. ePHI file upload area, drag-and-drop or browse. Index file upload area, drag-and-drop or browse. Subject area for transmitted message, optional. Comment/Body area for transmitted message, optional. Usage mode: Selector for automated multi-recipient mode. Selector for manual single recipient mode. Management Console access. Error Log access. Index Editor. Error checking indicator and Send control: upon upload of the ePHI documents and index files an error checking algorithm verifies that all required information for the multi-recipient transmission meets requirements. The control is inactive until all errors are remedied. Settings control: interface area which allows for the setting of transmission specific information (e.g., delay of send time).

The system 10 also allows a business user to receive patient medical records. Business user may be from the same vertical channel (i.e., Referring Doctor). Receive & Reply: the system 10 provides the ability for a business user to receive patient medical records, legal disclosures and any document or any file type (e.g., any digital document whether it is a written document, an image, an audio file, a video). It is assumed that the sender and receiver can read the exchanged information via commercially available software. The business user will receive an email. The email will contain a link to receiving URL. The business user will be able to open a link to this website, download the submitted document and save it in their local device (i.e., computer, phone). The link expires in a pre-configured time by the vertical initiator or the Send-TheDoc provider depending on the application. The reason for expiring is to minimize the risk of secure documents exposure on the cloud and also to maintain an agile computing environment that is responsive. The key innovation here is that the receiver will not need to remember any passwords. Should the sender wish to enhance the security, they can submit already encrypted documents (e.g., PDF with password that the user knows, for example the social security number or a combination of the last four of social security and the street address). Afterwards the business user may edit the submitted document, fill out certain fields, fill-out new forms, and then be ready to reply. REPLY—The business user will open the original email sent by the sender and will open again the link to the Receive-TheDoc™ website; the business user will upload the files to be communicated (via file browsing or dragging & dropping files to the designated area) to the original sender. Afterwards the business user may or may-not edit the email subject and comments (depending on Send-TheDoc configurations) and then select "REPLY" to send the documents in a secure and if needed HIPAA compliant manner (depending on the vertical).

Start a new user account for the same vertical. The receiving business user will be able to go to the www.Send-TheDoc.com website link (available in the Receive-TheDoc user interface) and will create a new account so that s/he is able to send documents to their extended enterprise (i.e., patients, labs, other Doctors, lawyers, accountants and so on)

Business user from other vertical channels (CPA, Lawyer, . . . ). Receive & Reply: the system 10 provides the ability for a business user to receive patient medical records, legal disclosures and any document or any file type (e.g., any digital document whether it is a written document, an image, an audio file, a video). It is assumed that the sender and receiver can read the exchanged information via commercially available software. The business user will receive an email. The email will contain a link to receiving URL. The business user will be able to open a link to this website, download the submitted document and save it in their local device (i.e., computer, phone). The link expires in a pre-configured time by the vertical initiator or the Send-TheDoc provider depending on the application. The reason for expiring is to minimize the risk of secure documents exposure on the cloud and also to maintain an agile computing environment that is responsive. Afterwards the business user may edit the submitted document, fill out certain fields, fill-out new forms, and then be ready to reply. REPLY—The business user will open the original email sent by the sender and will open again the link to the Receive-TheDoc™ website (see Additional Security Considerations Part1—1.11); the business user will upload the files to be communicated (via file browsing or dragging & dropping files to the designated area) to the original sender. Afterwards the business user may or may-not edit the email subject and comments (depending on Send-TheDoc configurations) and then select "REPLY" to send the documents in a secure and if needed HIPAA compliant manner (depending on the vertical).

Progress Indicators for the receiver: when the user downloads and uploads files there is an indicator showing the progress of the specific action. Once the "REPLY" button is selected an indicator displays that completion of the submission.

Start a new user account for a different vertical: the receiving business user will be able to go to the www.Send-TheDoc.com website link (available in the Receive-TheDoc user interface) and will have to identify if there is sponsored vertical that s/he can create a new account. If there is a sponsored vertical then the user can create a new account so that s/he is able to send documents to their extended enterprise (i.e., customers, colleagues, etc.). If a sponsored vertical does not exist, then they can use a general website (Anyone.Send-TheDoc.com) for a fee or complimentary contingent upon the Do-TheDocs policy at the time.

The system 10 also allows consumers to receive their medical records, legal disclosures and any document or any file type. Receive & Reply: the system 10 provides the ability for a user to receive their medical records, legal disclosures and any document or any file type (e.g., any digital document whether it is a written document, an image, an audio file, a video). It is assumed that the sender and receiver can read the exchanged information via commercially available software. The user will receive an email. The email will contain a link to receiving URL. The user will be able to open a link to this website link, download the submitted document and save it in their local device (i.e., computer, phone). The link expires in a pre-configured time by the vertical initiator or the Send-TheDoc provider depending on the application. The reason for expiring is to minimize the risk of secure documents exposure on the cloud and also to maintain an agile computing environment that is responsive. Afterwards the user may edit the submitted document, fill out certain fields and then be ready to reply. REPLY—The consumer will open the original email sent by the sender and will open again the link to the Receive-TheDoc™ website; the business user will upload the files to be communicated (via file browsing or dragging & dropping files to the designated area) to the original sender. Afterwards the consumer may or may-not edit the email subject and comments (depending on Send-TheDoc configurations) and then select "REPLY" to send the documents in a secure and if needed HIPAA compliant manner (depending on the vertical).

The system 10 also allows the receiver initiate secure communications with the vertical initiator. The receiver may initiate a "Secure Chat" session with the sender (e.g., their dentist or dental office) during business hours. This will ensure that the vertical initiator will be able to securely converse with its receivers instead of using texting which is not HIPAA compliant. The technology utilized to exchange secure chat is the same technology used for the encrypted document delivery. The receiver may also include a "Secure Note" during the document replying process. The secure note is encrypted and visible only from the sender or the receiver with access to Send-TheDoc or Receive-TheDoc.

The system 10 may also provide the promotional space to connect with vertical industry channel. Layout of promotional space—Tiles: the promotional space afforded to all vendors on the user display will be structured as a number of contiguous tiles (e.g., ranging from one to three tiles). There will be preconfigured and standardized layouts from which the vendor marketing specialist may choose from for their layout. There will be a customizable layout from which the vendor marketing specialist may build a layout with the supplied tools. For these custom layouts, optimization tools and algorithms will be available to assist the user in optimizing the promotion to the supported device types (e.g., smart phones vs. laptop display). Single Tile—a specific time slot is dedicated to a single vendor. Layered information (email, call-outs and balloon, etc.) on top of any tile or number of tiles. Increasing User Attraction: press releases, breaking news and related time-sensitive releases of information may be included in such overlays. Tools available: e.g., sephia, polarization, grid overlays, in general artistic artifacts.

The system 10 also allows business to connect with business vendors (B2B). These vendors have the innate need to connect with specific vertical industry channels (i.e., dental offices) and accomplish the following activities: Promote their vertical industry specific products and services (i.e., to the Dental office staff) and more specifically to decision influencers and makers (e.g., the Doctor and/or the office manager and/or the front desk. In the case of large practices with corporate headquarters the C-level executive and regional managers are the key persons to use this service to simultaneously share files and promote their practices.). In other verticals it is meant to promote products and services to the owners and/or decision makers (e.g., lawyer, real estate agent, office managers, coordinators, etc.). Educate the vertical businesses (i.e., dental offices) of existing, new and upcoming technologies (e.g., technologies that can automate patient care and administrative processes.) by means of case studies and/or white papers. Share product and service specifications and notifications (recalls) and possibly side-by-side comparisons that are generated by 3rd parties (and not the vendor themselves). Send-TheDoc could be that 3rd party. In addition, performance metrics (minimum, desired and optimum) for products and services can be shared with the targeted audience.

The displayed content is refereed before it is broadcasted. The refereed process filters content for the following criteria: inappropriate content, vertical specific content, competitive slander, and/or meets professional guidelines set forth by Send-TheDoc service.

The system 10 provides a promoter dashboard/control panel—Market-TheDoc. The promoter control panel (dashboard) will facilitate the following functions for the promoter: Purchase promotional space. Promotional space is classified under the following categories. Retainer for number of leads produced by: Global exposure, National exposure, State exposure, Regional exposure—Region being defined as a series of contiguous zip codes grouped by a functional rule (i.e., North, South, East West, Central, North-East, North-West, South-East, South-West), and/or Postal code (i.e., zip code).

The system 10 also generates time slot impressions including: Fixed fee time slot (independent of impressions) and Variable fee time slot (dependent on number of impressions), Bundled fee composite time slot with: fixed fee and/or variable fee. All time slot impressions are produced on a pre-specified daily timetable by geographic reach: National exposure, State exposure, Regional exposure—Region being defined as a series of contiguous zip codes grouped by a functional rule (i.e., North, South, East West, Central, North-East, North-West, South-East, South-West), and/or Postal code (i.e., zip code). For example, a variable mix of these impression could be that on a daily base there are two hours of National exposure slots (one in the morning and one in the afternoon) and the rest of the exposure will be at the regional level.

The system 10 may also track promotional views and generate viewer reports. The system may generate reports including tracked user usage by the following taxonomy: Viewer: Glimpse, Glance, Impression; Interested: Cursory, Typical, Significant, Detailed; Lead: Casual, Probable, Serious, Strong. Covered timeframe of reports include daily, weekly, monthly, quarterly, and/or annually.

For example, sponsorship impressions which are viewed by each user at the beginning of login in the following sequential manner: Gold—National level with a pre-specified exposure (e.g., 5-6 sec); Silver—National level with a pre-specified exposure (e.g., 4-5 sec); Bronze—National level with a pre-specified exposure (e.g., 3-4 sec); Regional level with a pre-specified exposure (e.g., 3-4 sec).

The system 10 may by configured and provide content for the purchased promotional space. Content types are classified as follows: Text; Images; Rich Media (animated gif); Video; Notifications (call-outs); Web page: Text, Voice, Text & voice; Mobile Application: Text, Voice, Text & voice; and/or Social media connectors.

Content layout is classified as follows: Main area can be organized in 1, 2 or 3 tiles. Multiple vendors can be incorporated (one for each tile). The auxiliary area is one tile. Any content type can be placed in the main or auxiliary area. Uploading and configuring content. Refereeing and publishing content.

View & Configure promotional space reports: Promotion Reach (impressions/views) as defined by the number of users exposed to a given promotion. Specific metrics of a viewing define different level of viewing intensity (as long as there is user activity) such as: 1-5 seconds—view classified as a glimpse, 5-10 seconds—view classified as an glance, More than 11 seconds—view classified as an impression. Promotion Interest. Promotion Purchasing interest.

The system 10 also allows business to connect with consumer vendors (B2C). These vendors have the innate need to connect with specific vertical industry channels (i.e., patients, consumers) and accomplish the following activities: Promote their vertical industry specific products and services (e.g., dental hygiene products). Educate consumers (i.e., dental offices) of existing, new and upcoming products and services (e.g., electric tooth brushes, dental whitening.) by means of case studies and/or white papers. Share product and service specifications and notifications (recalls) and possibly side-by-side comparisons that are generated by 3rd parties (and not the vendor themselves). Receive-TheDoc could be that 3rd party. In addition, performance metrics (minimum, desired and optimum) for products and services can be shared with the targeted audience.

The displayed content is refereed before it is broadcasted. The refereed process filters content for the following criteria: Inappropriate content, Vertical specific content, Competitive slander, and/or Determination of meeting professional guidelines set forth by Receive-TheDoc service.

The system 10 provides a Promoter Dashboard/Control Panel—Market-TheDoc. The promoter control panel (dashboard) will facilitate the following functions for the promoter: Purchase promotional space. Promotional space is classified under the following categories. Retainer for number of leads produced by: National exposure, State exposure, Regional exposure—Region being defined as a series of contiguous zip codes grouped by a functional rule (i.e., North, South, East West, Central, North-East, North-West, South-East, South-West), Postal code (i.e., zip code). Time slot impressions: Fixed fee time slot (independent of impressions), Variable fee time slot (dependent on number of impressions), Bundled fee composite time slot with: Fixed fee and/or Variable fee. All time slot impressions are produced on a pre-specified daily timetable by geographic reach: National exposure, State exposure, Regional exposure—Region being defined as a series of contiguous zip codes grouped by a functional rule (i.e., North, South, East West, Central, North-East, North-West, South-East, South-West), and/or Postal code (i.e., zip code). For example, a variable mix of these impression could be that on a daily base there are two hours of National exposure slots (one in the morning and one in the afternoon) and the rest of the exposure will be at the regional level.

The system 10 also generates reports including tracking user usage by the following taxonomy: Viewer: Glimpse, Glance, Impression; Interested: Cursory, Typical, Significant, Detailed; Lead: Casual, Probable, Serious, Strong. Covered timeframe of reports include daily, weekly, monthly, quarterly, and/or annually.

Sponsorship impressions which are viewed by each user at the beginning of viewing in the following sequential manner: Vertical initiator promotion with a pre-specified exposure (e.g., 30-120 sec); Gold—National level with a pre-specified exposure (e.g., 5-6 sec); Silver—National level with a pre-specified exposure (e.g., 4-5 sec); Bronze—National level with a pre-specified exposure (e.g., 3-4 sec); and/or Regional level with a pre-specified exposure (e.g., 3-4 sec).

The system 10 may configure and provide content for the purchased promotional space. Content types are classified as follows: Text, Images, Rich Media (animated gif), Video, Notifications (call-outs), Coupons & promotional discounts, Web page: Text, Voice, Text & voice; Mobile Application: Text, Voice, Text & voice; and/or Social media connectors.

Content layout is classified as follows: Main area can be organized in 1, 2 or 3 tiles. Multiple vendors can be incorporated (one for each tile). The auxiliary area is one tile. Any content type can be placed in the main or auxiliary area. Uploading and configuring content: Refereeing and publishing content.

View & Configure promotional space reports: Promotion Reach (impressions/views) as defined by the number of users exposed to a given promotion. Specific metrics of a viewing define different level of viewing intensity (as long as there is user activity) such as: 1-5 seconds—view classified as a glimpse, 5-10 seconds—view classified as an glance, More than 11 seconds—view classified as an impression, promotion interest, and/or promotion purchasing interest.

The system 10 also provides information to the consumer. For example, promotion of products specific to the vertical industry (e.g., dental hygiene, etc. . . . ). Educational materials to assist consumers to continuously update their knowledge with latest dental hygiene products, services and techniques. Benchmarks/comparisons/performance metrics of similar products or services (e.g., comparison of product technical specifications or services, best-in-class product benchmarks).

Promoter accessibility by the vertical initiator via the following means: Indicate product/service interest for the information displayed by selecting: To download & view product/service specifications, To view the vendor website, The "Sponsors" link to indicate interest of finding who is sponsoring the Do-TheDocs™ service, To bookmark the current displayed vendor promotion, To scroll back to find information displayed earlier during the day, To select "Share" so that they can share the current link with other professionals via email, Select social media connections (e.g., like for facebook), Complete vendor product/service surveys, Case studies/white papers, and/or Search for subjects in: Receive-TheDoc promoters with the ability to sort results: Alphabetically, By time slot proximity, By highest interest, By promotion investment level; Over the open internet.

The system 10 also allows the users to request notifications such as, notify me for new product updates, for new educational material, for promotions, for press releases, for product recalls. User may indicate purchasing interest by selecting: The "Contact us" link to contact the vendor, the "Contact me" link to provide contact information so that the vendor can contact the vertical initiator via email, txt or voice, and/or the "Chat" link to initiate a chat with the vendor that is currently being displayed. The system 10 may also associate the consumer behavior to the vendor promotion via a unique displayed promotion code to enable analytics to assist the specific vendor in determining promotion effectiveness, overall product interest and subsequently define an indicator for sales forecast.

A controller, computing device, server or computer, such as described herein, includes at least one or more processors or processing units and a system memory (see above). The controller typically also includes at least some form of computer readable media. By way of example and not limitation, computer readable media may include computer storage media and communication media. Computer storage media may include volatile and nonvolatile, removable and non-removable media implemented in any method or technology that enables storage of information, such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer readable media.

The order of execution or performance of the operations in the embodiments of the invention illustrated and described herein is not essential, unless otherwise specified. That is, the operations described herein may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In some embodiments, a processor, as described herein, includes any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term processor.

In some embodiments, a database, as described herein, includes any collection of data including hierarchical databases, relational databases, flat file databases, object-relational databases, object oriented databases, and any other structured collection of records or data that is stored in a computer system. The above examples are exemplary only, and thus are not intended to limit in any way the definition and/or meaning of the term database. Examples of databases include, but are not limited to only including, Oracle® Database, MySQL, IBM® DB2, Microsoft® SQL Server, No SQL, Sybase®, and PostgreSQL. However, any database may be used that enables the systems and methods described herein. (Oracle is a registered trademark of Oracle Corporation, Redwood Shores, Calif.; IBM is a registered trademark of International Business Machines Corporation, Armonk, N.Y.; Microsoft is a registered trademark of Microsoft Corporation, Redmond, Wash.; and Sybase is a registered trademark of Sybase, Dublin, Calif.)

The above description of illustrated examples of the present invention, including what is described in the Abstract, are not intended to be exhaustive or to be limitation to the precise forms disclosed. While specific embodiments of, and examples for, the invention are described herein for illustrative purposes, various equivalent modifications are possible without departing from the broader spirit and scope of the present invention.

What is claimed is:

1. A networked computer system for transmitting information to users via a website or mobile application, comprising:
a database including:
a plurality of user account records including vertical initiator user account records and recipient user account records, the vertical initiator user account records having information associated with corresponding vertical initiator users including vertical initiator location identifiers and a plurality of recipient types, each recipient user account records including recipient addresses and recipient types; and a plurality of promotional records including promotional information associated with the recipient types and geographic location; and a server including a processor programmed to:

receive a transmittal request, from a vertical initiator user via a first user computing device, to transmit a communication message to a recipient address and, upon receiving the transmittal request:

access a vertical initiator user account record associated with the vertical initiator user;

select a plurality of recipient types included in the vertical initiator user account record; and display a messaging window on the first user computing device including a recipient address input bar for receiving a recipient email address and a plurality of user selectors associated with each of the selected plurality of recipient types, each of the user selectors being selectable by the virtual initiator user;

upload a data file received from vertical initiator user to be transmitted with the communication message and generate and store a corresponding file record including the uploaded data file;

receive input from the vertical initiator user via the messaging window including the recipient address and a selection of a recipient type associated with the recipient address and responsively generate a unique communication identifier including information indicative of the selected recipient type, the uploaded data file, and the communication message;

generate a corresponding recipient user account record including the recipient address received from the vertical initiator user, the selected recipient type, and a vertical initiator location identifier associated with the vertical initiator user, the vertical initiator location identifier indicating a geographic location associated with the vertical initiator user;

generate and transmit a notification message including the unique communication identifier to the recipient address;

receive a display request to display the communication message in response to a recipient user accessing the unique communication identifier via a second user computing device, the display request including information indicating the selected recipient type and the communication message associated with the unique communication identifier, and a recipient location identifier associated with the second user computing device, the recipient location identifier indicating a geographic location of the second user computing device;

access the plurality of promotions records being stored in the database and select promotional information associated with the recipient type and the recipient location identifier;

determine whether the recipient location identifier matches the vertical initiator location identifier included in the corresponding recipient user account record; and upon determining the recipient location identifier matches the vertical initiator location identifier included in the corresponding recipient user account record:

display a webpage including the communication message and the selected promotional information via the second user computing device; and the recipient user downloading the data file to the second user computing device via the displayed webpage.

2. A system in accordance with claim 1, wherein the processor programmed to display location-based promotional information in a regional area of the webpage and display recipient type-based promotional information in a recipient area.

3. A system in accordance with claim 2, wherein the processor is programmed to display a recipient verification request on the second user computing device upon determining the recipient location identifier is different than the location identifier associated with the vertical initiator user included in the corresponding recipient user account record.

4. A system in accordance with claim 1, the unique communication identifier including information associated with the vertical initiator user, the processor programmed to determine and display promotional information associated with the vertical initiator user in response to receiving the display request.

5. A system in accordance with claim 1, the processor programmed to select a recipient type based on the recipient address entered by the vertical initiator user and display the messaging window indicating the selected recipient type.

6. A system in accordance with claim 1, the processor programmed to:

detect recipient activity associated with the displayed promotional information; and determine a viewer interest value indicative of the associated recipient activity value; and display the viewer interest value to the vertical initiator user via the first user computing device to illustrate the effectiveness of the promotional information being displayed on the webpage.

7. A system in accordance with claim 1, the processor programmed to:

receive a list of vertical initiator users from a $3^{rd}$ party server in response to transmitting a verification request to the $3^{rd}$ party server; and determine if the vertical initiator user is included in a list of initiator users and responsively generate and transmit the transmittal message.

8. A system in accordance with claim 1, the transmittal request including a location identifier associated with the vertical initiator user, the processor programmed to determine if the received location identifier matches a location information included in a corresponding user record associated with the vertical initiator user, and responsively generate and transmit the transmittal message.

9. A system in accordance with claim 8, the processor programmed:

display a verification request to the vertical initiator user upon determining the received location identifier is different than the location information included in the corresponding user record;

receive a validation identifier in response to the verification request; and generate and transmit the transmittal message if the received validation identifier matches a validation identifier included in a user record associated with the vertical initiator.

10. A system in accordance with claim 1, the processor programmed to:

detect recipient activity associated with the displayed promotional information; and determine a viewer interest value indicative of the associated recipient activity value.

11. A method of operating a networked computer system for transmitting information to users via a website or mobile application, the networked computer system including a server computer including a processor, the method including the processor performing the steps of:
receiving a transmittal request, from a vertical initiator user via a first user computing device, to transmit a communication message to a recipient address and, upon receiving the transmittal request:
accessing a vertical initiator user account record associated with the vertical initiator user being stored in a database, the vertical initiator user account record including information associated with the corresponding vertical initiator user including a vertical initiator location identifier and a plurality of recipient types, the vertical initiator location identifier indicating a geographic location associated with the vertical initiator user;
selecting a plurality of recipient types included in the vertical initiator user account record; and
displaying a messaging window on the first user computing device including a recipient address input bar for receiving a recipient email address and a plurality of user selectors associated with each of the selected plurality of recipient types, each of the user selectors being selectable by the virtual initiator user;
uploading a data file received from vertical initiator user to be transmitted with the communication message and generate and store a corresponding file record including the uploaded data file;
receiving input from the vertical initiator user via the messaging window including the recipient address and a selection of a recipient type associated with the recipient address and responsively generate a unique communication identifier including information indicative of the selected recipient type, the uploaded data file, and the communication message;
generate a recipient user account record including the recipient address received from the vertical initiator user, the selected recipient type, and the vertical initiator location identifier associated with the vertical initiator user;
generating and storing a notification message including the unique communication identifier in a database, and transmitting the notification message to the recipient address;
receiving a display request to display the communication message in response to a recipient user accessing the unique communication identifier via a second user computing device, the display request including information indicating the selected recipient type and the communication message associated with the unique communication identifier, and a recipient location identifier associated with the second user computing device, the recipient location identifier indicating a geographic location of the second user computing device;
accessing a plurality of promotions records being stored in the database including promotional information associated with the recipient types and geographic location and selecting promotional information associated with the selected recipient type and the recipient location identifier;
determine whether the recipient location identifier matches the vertical initiator location identifier included in the corresponding recipient user account record; and upon determining the recipient location identifier matches the vertical initiator location identifier included in the corresponding recipient user account record:
displaying a webpage including the communication message and the selected promotional information via the second user computing device; and
downloading the data file to the second user computing device via the displayed webpage.

12. A method in accordance with claim 11, including the steps of:
displaying location-based promotional information in a regional area of the webpage and display recipient type-based promotional information in a recipient area.

13. A method in accordance with claim 12, including the step of
displaying a recipient verification request on the second user computing device upon determining the recipient location identifier is different than the location identifier associated with the vertical initiator user included in the recipient user account record.

14. A method in accordance with claim 11, including the steps of:
generating the unique communication identifier including information associated with the vertical initiator user; and
displaying promotional information associated with the vertical initiator user in response to receiving the display request.

15. A method in accordance with claim 11, including the steps of:
selecting a recipient type based on the recipient address entered by the vertical initiator user and displaying the messaging window indicating the selected recipient type.

16. A method in accordance with claim 11, including the steps of:
detecting recipient activity associated with the displayed promotional information; and
determining a viewer interest value indicative of the associated recipient activity value; and
displaying the viewer interest value to the vertical initiator user via the first user computing device to illustrate the effectiveness of the promotional information being displayed on the webpage.

17. A method in accordance with claim 11, including the steps of:
receiving a list of vertical initiator users from a $3^{rd}$ party server in response to transmitting a verification request to the $3^{rd}$ party server; and
determining if the vertical initiator user is included in a list of initiator users and responsively generating and transmitting the transmittal message.

18. A method in accordance with claim 11, including the steps of:
receiving the transmittal request including a location identifier associated with the vertical initiator user; and
determining if the received location identifier matches a location information included in a corresponding user record associated with the vertical initiator user, and responsively generating and transmitting the transmittal message.

19. A method in accordance with claim 11, including the steps of:
determining recipient activity associated with the displayed promotional message; and
determining a viewer interest value indicative of the associated recipient activity value.

20. One or more non-transitory computer-readable storage media, having computer-executable instructions embodied thereon, wherein when executed by at least one processor, the computer-executable instructions cause the processor to:

receive a transmittal request, from a vertical initiator user via a first user computing device, to transmit a communication message to a recipient address and, upon receiving the transmittal request:

accessing a vertical initiator user account record associated with the vertical initiator user being stored in a database, the vertical initiator user account record including information associated with the corresponding vertical initiator user including a vertical initiator location identifier and a plurality of recipient types, the vertical initiator location identifier indicating a geographic location associated with the vertical initiator user;

selecting a plurality of recipient types included in the vertical initiator user account record; and displaying a messaging window on the first user computing device including a recipient address input bar for receiving a recipient email address and a plurality of user selectors associated with each of the selected plurality of recipient types, each of the user selectors being selectable by the virtual initiator user;

upload a data file received from vertical initiator user to be transmitted with the communication message and generate and store a corresponding file record including the uploaded data file;

receive input from the vertical initiator user via the messaging window including the recipient address and a selection of a recipient type associated with the recipient address and responsively generate a unique communication identifier including information indicative of the selected recipient type, the uploaded data file, and the communication message;

generate a corresponding recipient user account record including the recipient address received from the vertical initiator user, the selected recipient type, and the vertical initiator location identifier associated with the vertical initiator user;

generate and transmit a notification message including the unique communication identifier to the recipient address;

receive a display request to display the communication message in response to a recipient user accessing the unique communication identifier via a second user computing device, the display request including information indicating the selected recipient type and the communication message associated with the unique communication identifier, and a recipient location identifier associated with the second user computing device, the recipient location identifier indicating a geographic location of the second user computing device; and access a plurality of promotions records being stored in the database including promotional information associated with the recipient types and geographic location and select promotional information associated with the selected recipient type and the recipient location identifier;

determine whether the recipient location identifier matches the vertical initiator location identifier included in the corresponding recipient user account record; and upon determining the recipient location identifier matches the vertical initiator location identifier included in the corresponding recipient user account record:

display a webpage including the communication message and the selected promotional information via the second user computing device; and the recipient user downloading the data file to the second user computing device via the displayed webpage.

\* \* \* \* \*